(12) United States Patent
Zin et al.

(10) Patent No.: US 9,807,543 B2
(45) Date of Patent: Oct. 31, 2017

(54) ELECTRONIC TEST DEVICE DATA COMMUNICATION

(71) Applicant: Z-INTEGRATED DIGITAL TECHNOLOGIES, INC., San Diego, CA (US)

(72) Inventors: Benedict L. Zin, San Diego, CA (US); Andy Sturman, San Diego, CA (US); Albert R. Nazareth, Mercerville, NJ (US)

(73) Assignee: Z-INTEGRATED DIGITAL TECHNOLOGIES, INC., San Diego, CA (US)

( * ) Notice: Subject to any disclaimer, the term of this patent is extended or adjusted under 35 U.S.C. 154(b) by 115 days.

(21) Appl. No.: 14/690,156

(22) Filed: Apr. 17, 2015

(65) Prior Publication Data
US 2015/0301031 A1    Oct. 22, 2015

Related U.S. Application Data

(60) Provisional application No. 61/980,775, filed on Apr. 17, 2014.

(51) Int. Cl.
*H04W 4/00* (2009.01)
*G01N 21/77* (2006.01)
(Continued)

(52) U.S. Cl.
CPC .......... *H04W 4/008* (2013.01); *A63F 13/327* (2014.09); *A63F 13/52* (2014.09); *G01N 27/02* (2013.01);
(Continued)

(58) Field of Classification Search
CPC ............... G01N 21/78; G01N 21/8483; G01N 2201/0221; G01N 27/02; G01N 33/48; G01N 33/48792; G01N 33/52; H04B 1/3833; H04W 4/008; H04W 84/18
USPC .... 436/63, 65, 164, 165, 169; 422/400, 420, 422/430, 82.05; 702/19; 435/287.7, 435/288.7
See application file for complete search history.

(56) References Cited

U.S. PATENT DOCUMENTS 6,966,880 B2   11/2005   Boecker et al.
7,044,911 B2    5/2006   Drinan et al.
(Continued)

FOREIGN PATENT DOCUMENTS

CN   103105372 A   5/2013
CN   202920245 U   5/2013
(Continued)

OTHER PUBLICATIONS

International Search Report and Written Opinion for PCT Application No. PCT/US15/26528, mailed Sep. 2, 2015, which corresponds to this present application.

*Primary Examiner* — Maureen Wallenhorst
(74) *Attorney, Agent, or Firm* — Knobbe, Martens, Olson & Bear

(57) ABSTRACT

Electronic test devices and methods include data transfer capabilities. In one implementation, an assay device includes wireless communication capabilities to send assay result decisions and/or values to a separate processing and display device such as a smartphone. In another implementation, light sources are modulated both for performing an assay and encoding and transmitting a result of an assay.

11 Claims, 17 Drawing Sheets

(51) Int. Cl.
    *G01N 27/02*     (2006.01)
    *G01N 33/48*     (2006.01)
    *H04W 84/18*     (2009.01)
    *G01N 33/487*     (2006.01)
    *A63F 13/327*     (2014.01)
    *A63F 13/52*     (2014.01)
    *H04M 1/725*     (2006.01)
    *H04B 1/3827*     (2015.01)
    *G01N 21/78*     (2006.01)
    *G01N 21/84*     (2006.01)
    *G06F 3/0482*     (2013.01)
    *H04W 12/08*     (2009.01)

(52) U.S. Cl.
    CPC .. *G01N 33/48792* (2013.01); *H04M 1/72519* (2013.01); *A63F 2300/405* (2013.01); *G01N 21/77* (2013.01); *G01N 21/78* (2013.01); *G01N 21/8483* (2013.01); *G01N 2201/0221* (2013.01); *G06F 3/0482* (2013.01); *H04B 1/3833* (2013.01); *H04W 12/08* (2013.01); *H04W 84/18* (2013.01)

(56) References Cited

U.S. PATENT DOCUMENTS

| | | | |
|---|---|---|---|
| 7,214,542 B2 | 5/2007 | Hutchinson | |
| 7,220,597 B2 | 5/2007 | Zin et al. | |
| 7,499,170 B2 | 3/2009 | Sasaki et al. | |
| 7,515,833 B2 | 4/2009 | Way | |
| 7,575,558 B2 | 8/2009 | Boecker et al. | |
| 7,920,907 B2 | 4/2011 | McGarraugh et al. | |
| 8,126,728 B2 | 2/2012 | Dicks et al. | |
| 8,226,905 B2 | 7/2012 | Abdallah | |
| 8,372,351 B2 | 2/2013 | Ow-Wing et al. | |
| 8,419,636 B2 | 4/2013 | Brown et al. | |
| 8,545,437 B2 | 10/2013 | Sakata et al. | |
| 8,663,103 B2 | 3/2014 | Causey et al. | |
| 8,679,407 B2 | 3/2014 | Holmes et al. | |
| 8,696,597 B2 | 4/2014 | Neel et al. | |
| 8,737,971 B2 | 5/2014 | Van Rooyen et al. | |
| 8,889,424 B2 | 11/2014 | Ehrenkranz et al. | |
| 8,895,315 B2* | 11/2014 | Batman | G08C 17/02 128/903 |
| 8,932,250 B2 | 1/2015 | Montgomery et al. | |
| 9,041,538 B2 | 5/2015 | Peeters et al. | |
| 9,047,648 B1 | 6/2015 | Lekutai et al. | |
| 9,065,720 B2 | 6/2015 | Allen et al. | |
| 9,086,417 B2 | 7/2015 | Khattak et al. | |
| 9,133,024 B2 | 9/2015 | Phan et al. | |
| 2007/0257197 A1 | 11/2007 | Gordon et al. | |
| 2010/0305421 A1* | 12/2010 | Ow-Wing | A61B 5/0002 600/365 |
| 2010/0331645 A1* | 12/2010 | Simpson | A61B 5/0002 600/347 |
| 2012/0083044 A1* | 4/2012 | Sturman | G01N 21/8483 436/165 |
| 2013/0040401 A1 | 2/2013 | Zin et al. | |
| 2013/0244339 A1 | 9/2013 | Ehrenkranz et al. | |
| 2013/0273528 A1 | 10/2013 | Ehrenkranz et al. | |
| 2013/0276521 A1* | 10/2013 | Fuerst | G01N 33/493 73/61.59 |
| 2013/0332196 A1 | 12/2013 | Pinker | |
| 2014/0051958 A1* | 2/2014 | Fern | G01N 33/48792 600/365 |
| 2014/0322815 A1 | 10/2014 | Carlsgaard et al. | |
| 2015/0021207 A1 | 1/2015 | Kyung et al. | |
| 2015/0207796 A1 | 7/2015 | Love et al. | |
| 2015/0244852 A1 | 8/2015 | Erickson et al. | |
| 2015/0309008 A1 | 10/2015 | Adelman et al. | |

FOREIGN PATENT DOCUMENTS

| | | |
|---|---|---|
| CN | 203981683 U | 12/2014 |
| WO | 2014197604 A2 | 12/2014 |
| WO | 2014201451 A1 | 12/2014 |
| WO | 2015140597 A1 | 9/2015 |

\* cited by examiner

ELECTRONIC TEST DEVICE DATA COMMUNICATION

CROSS-REFERENCE TO RELATED APPLICATIONS

The present application claims the benefit of U.S. Provisional Patent Application Ser. No. 61/980,775, filed Apr. 17, 2014 and entitled "TESTING DEVICE CONNECTIVITY," which is hereby expressly incorporated by reference in its entirety. Furthermore, any and all priority claims identified in the Application Data Sheet, or any correction thereto, are hereby incorporated by reference under 37 C.F.R. §1.57.

FIELD

The present application generally relates to data communications to and from electronic test devices and corresponding methods of data communication.

BACKGROUND

With ever increasing health care costs, hand-held or otherwise portable test kits, typically either wholly disposable or with disposable parts, have become a popular, low-cost alternative to expensive visits to a specialized health care provider and/or time consuming laboratory testing. Tests related to conditions such as pregnancy, fertility, and diabetes (to name only a few), may be quickly and accurately performed in home. Test devices may also be used at a point of care (e.g., lab bench readers) to provide quick results. The test devices may also be used in the field such as in remote areas where the time to take a sample and have it delivered for testing may make accurate testing impractical and/or expensive. For example, a camper may have little time to assess the severity of a hiking companion's wound. A myotoxin or aflatoxin test device may be carried in a backpack and used to quickly determine whether immediate assistance is needed (e.g., venomous snake bite), or a more measured response is called for (e.g., standard first aid). Useful test devices such as these are not limited to health condition testing. Test devices for environmental conditions such as mold, toxins, bacterial contamination or other types of pests may be implemented for field use.

Test devices of this nature may collect and/or generate a variety of different types of data. In many cases, LEDs or other light sources internal to the devices illuminate samples of interest and/or regions where chemical reactions occur, and the absorbance, reflectivity, fluorescence, or other optical characteristic of the sample and/or region is detected with photodiodes, CCD arrays, or other light sensors. The output of the sensors is typically indicative of the presence and/or amount of a substance in a sample. Although optical interrogation techniques are common, other detection methods that sense current or impedance are also sometimes used. The results obtained when the test is used are often displayed to the user as an output in the form of illuminated LEDs or a small LCD display screen. Expanding the usefulness of these devices, especially with minimal cost increases, is desirable.

SUMMARY

The systems, methods, and devices of the disclosure each have several innovative aspects, no single one of which is solely responsible for the desirable attributes disclosed herein.

In one implementation, a test device comprises a sample inlet and assay electronics configured for conducting an assay to generate an assay result indicating the presence, absence, amount, degree, or severity of a chemical, physical, biological, medical, or environmental condition from a sample of material provided to the sample inlet. The assay electronics includes a light source configured to emit light under control of the assay electronics during and as part of conducting the assay. Also, the assay electronics is configured to cause the light source to emit a modulated light intensity encoding assay measurement data and/or an assay result derived from the assay measurement data.

In another implementation, a test device comprises a processor, a variable intensity light display, and means for conducting an assay to generate a result indicating the presence or absence of a substance contained in a sample provided via a test strip. The means for conducting the assay is in data communication with the processor, and the processor is configured to cause display of a human readable indication of the result via the variable intensity light display; and cause the variable intensity light display to emit a modulated light intensity encoding the result.

In another implementation, an assay system comprises a test device comprising a housing with an opening for inserting a test stick, a processor in the housing, and a variable intensity light source in the housing. The processor is configured to control an intensity level of the variable intensity light source, and modulates the variable intensity light source to both conduct an assay and encode a value related to an assay result or assay measurements.

In another implementation, a method of performing an assay and delivering the results thereof comprises detecting, via a photodetector, a quantity of light emitted from a light source that is reflected from a reagent reaction region, generating a result of the assay with the detecting, and modulating an intensity of light emitted by the light source to provide an encoding of the result of the assay.

In another implementation, a test device comprises assay electronics configured for conducting an assay to generate an assay result indicating the presence, absence, amount, degree, or severity of a chemical, physical, biological, medical, or environmental condition from a sample of material provided to the test device, a wireless transmitter coupled to the assay electronics, wherein the assay electronics is configured to generate assay measurement data and process that assay measurement data into a single assay result, and wherein the assay electronics is configured to send the single assay result to the wireless transmitter and wirelessly transmit the single assay result to an external processing and display device separate from the test device.

In another implementation, a method of testing comprises establishing a wireless communication channel between a test device in a first housing and a display device in a physically separate second housing, receiving a sample for testing at the test device, detecting, at the test device, a test timer initiation event, transmitting a test initiation message from the test device to the display device, in response to receiving the test initiation message, initiating and displaying a timer on the display device configured to identify an end time for the testing, upon the end time for the testing, obtaining a result of the testing at the display device from the test device, and displaying the received result on the display device.

In another implementation, a testing system comprises a test device including a processor, means for receiving a test stick, means for conducting an assay configured to detect a test timer initiation event and generate a result indicating the presence or absence of a substance contained in a sample provided via a test stick received via the means for receiving a test stick. The testing system further comprises a first wireless transceiver configured to transmit a test initiation message using the test timer initiation event via a communication channel and transmit the test result via the communication channel. The testing system further comprises a display device including a second wireless transceiver configured to establish the communication channel with the test device, receive the test initiation message from the test device via the communication channel and receive the test result from the test device. Also provided is a timer, wherein the timer is started in response to receiving the test initiation message, and a display configured to in response to establishing the communication channel, display a connection status message and display a value of the timer.

In another implementation, a handheld, single use, disposable chemical assay device comprises a housing, assay electronics contained within the housing, a display coupled to the housing and the assay electronics configured to display a result of the assay received from the assay electronics, and a wireless transmitter contained within the housing configured to send the result of the assay to an external processing and display device.

Details of one or more implementations of the subject matter described in this specification are set forth in the accompanying drawings and the description below. Other features, aspects, and advantages will become apparent from the description, drawings, and claims. Note that the relative dimensions of the following figures may not be drawn to scale.

DETAILED DESCRIPTION

Various aspects of communication features for an electronic test device are described which provide data transfer capabilities that extend beyond the test device. The data obtained from the test device can be transferred or transmitted such as to a personal computer, tablet, smartphone, or a receiver hub. The various different communication features described in further detail below can be incorporated into the test device to provide reliable data connectivity with little to no increase to the manufacturing cost of the test device. For example, in some implementations, the test device may be a one-time-use device. Accordingly, a need exists to provide data communication capabilities at an efficient (e.g., power, cost, speed, size) level.

Figure 1:
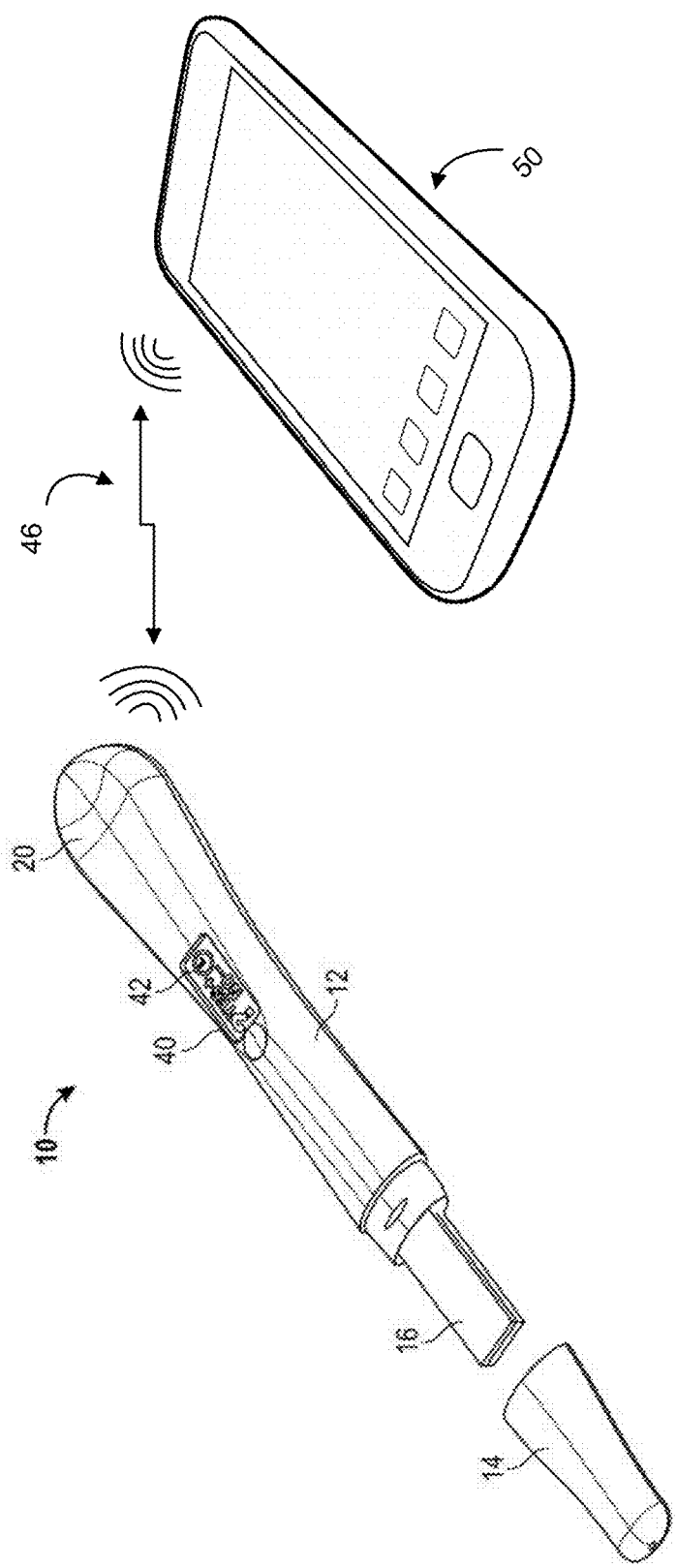
FIG. 1 is a perspective view of an example of a test device in wireless communication with an external processing and display device according to an implementation of the invention.

FIG. 1 shows a perspective view of an exemplary test device 10, in this case a lateral flow assay device. In this implementation, the device 10 includes a cap 14. The device also comprises an outer, molded casing 12 which defines a hollow, elongate enclosure. Casing 12 is configured to provide a recessed portion 20 shaped to permit users to place their thumb into the recessed portion and their forefinger on the bottom of the casing 12 to securely hold the device 10. A central section on the top of the casing 12 defines a centrally located window 40 which permits a user to observe test results. Inside the casing 12 is a lateral flow test strip and electronic components, details of one example of which will be described further below. Casing 12 holds a sample receiving member 16 onto which a fluid sample can be applied to the test strip in the device 10. The removable cap 14 can be secured to one end of the casing enclosure over the sample receiving member 16. Sample receiving member 16 is positioned so that part of the sample receiving member is received in the casing enclosure and part of the sample receiving member 16 extends from the end of the casing enclosure. In this embodiment, color or reflectivity changes are sensed electronically, and the results are presented to a user on a display 42. The display 42 may render various icons or messages to a user, such as test results, device status, or error messages. The display 42 may be color or monochrome. In one embodiment, the display 42 is a liquid crystal display (LCD).

As shown in FIG. 1, the test device 10 of FIG. 1 is in wireless communication with an external processing and display device 50 over a wireless communication channel 46. In the implementation of FIG. 1, the external processing and display device 50 is a "smart phone," which is typically a hand-held computing device including a touchscreen display and/or a keypad for user interaction and at least one wireless communication capability. In many cases, the external processing and display device 50 will include multiple types of wireless communication capabilities, potentially including several of Bluetooth™ (e.g., IEEE 802.15), Low Energy Bluetooth™ (e.g., IEEE 802.15.4), near-field communication (NFC) transceiver (e.g., ISO/IEC 18000-3 and/or ISO/IEC 14443 compliant configurations), wireless LAN (e.g. WiFi IEEE 802.11), and cellular telephone capabilities (e.g. 3G, 4G, LTE, etc.). The external processing and display device 50 is advantageously portable, such as a smartphone or tablet computer, but may be a stationary personal computer in some implementations.

To establish the wireless communication channel 46 between the test device 10 and the external processing and display device 50, the test device may include a wireless transceiver configured to communicate with the external processing and display device 50 in accordance with a communication protocol compatible with the capabilities of the external processing and display device 50, with Bluetooth™ and NFC being advantageous specific examples. For example, a wirelessly enabled microcontroller, with built-in low energy Bluetooth™ (e.g., IEEE 802.15.4 compliant) may be integrated in the circuit to enable data to be transmitted wirelessly to a Bluetooth™ (e.g., IEEE 802.15 compliant) enabled external processing and display device 50 such as a smartphone, a tablet, a PC, or the like.

FIG. 2A shows a perspective view of an alternative exemplary test device 100. This implementation is similar to the test device 10 illustrated in FIG. 1, but in this implementation the test strip is provided in a removable housing of its own, with the combination referred to herein as a "test stick." In this implementation, the device 100 includes a test stick acceptor port 110. The test stick acceptor port is designed to receive test sticks for analysis. The device 100 also includes a display 120. The display 120 may render various icons or messages to a user such as test results, device status, or error messages. The display 120 may be color or monochrome. In an example implementation, the display 120 may be a liquid crystal display (LCD). The device 100 may further include a test stick alignment marker 130. In the example shown, the test stick alignment marker 130 is a triangle pointing to the test stick acceptor 110. The test stick alignment marker aids with insertion of a test stick into the device 100. The device 100 may include a test stick ejector 140. The test stick ejector 140 may be a manual or electronic mechanism to eject a previously inserted test stick from the device 100.

FIG. 2B shows another perspective view of an exemplary digital detection device with a disposable test stick inserted therein. In the example shown, the device 100 is accepting a test stick assembly 200 housing the actual test strip 210. It is desirable for the test stick assembly 200 to couple with the device 100 so that the test stick assembly 200 will not fall out of the device 100 and may form a water resistant seal to protect a portion of the device 100 from fluid samples collected via the test stick assembly 200. The coupling should also minimize ambient light leakage into the device when testing is being performed on a test strip. Fluid samples collected via the test stick assembly 200 are generally urine, although depending on the test being performed, could be blood, sweat, tears, saliva, or any bodily fluid. The test stick assembly includes a test stick housing 220. In an implementation, the test stick housing 220 may be formed from plastic. The test stick assembly 200 includes a test stick alignment marker 230 corresponding with the test stick alignment marker 130 on the device 100. The test stick assembly 200 may also include a clicking sound feature to indicate proper alignment and insertion into device 100.

As with the device 10 of FIG. 1, the test device 100 of FIGS. 2A and 2B may include a wireless transceiver configured to communicate with an external processing and display device in accordance with a communication protocol compatible with the capabilities of the external processing and display device, with Bluetooth™ and NFC being advantageous specific examples. Generally, the test device 10 shown in FIG. 1 is a single use disposable device, whereas in the implementation of FIGS. 2A and 2B, the device 100 may be re-used with multiple single use disposable test sticks 200.

Figure 2:
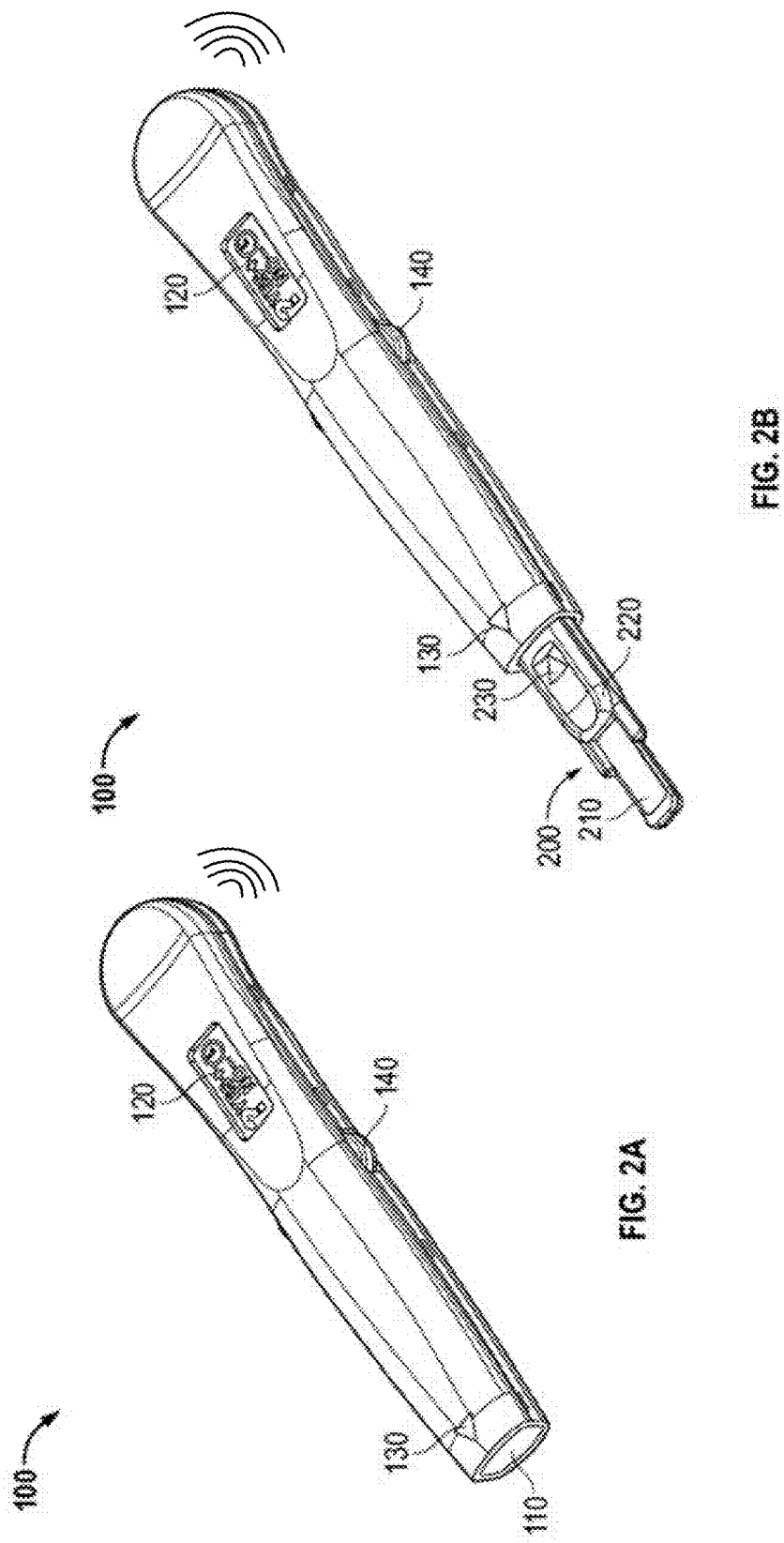
FIG. 2A is a perspective view of an alternative exemplary test device.
FIG. 2B shows another perspective view of an exemplary digital detection device with a disposable test stick inserted therein.
Figure 3:
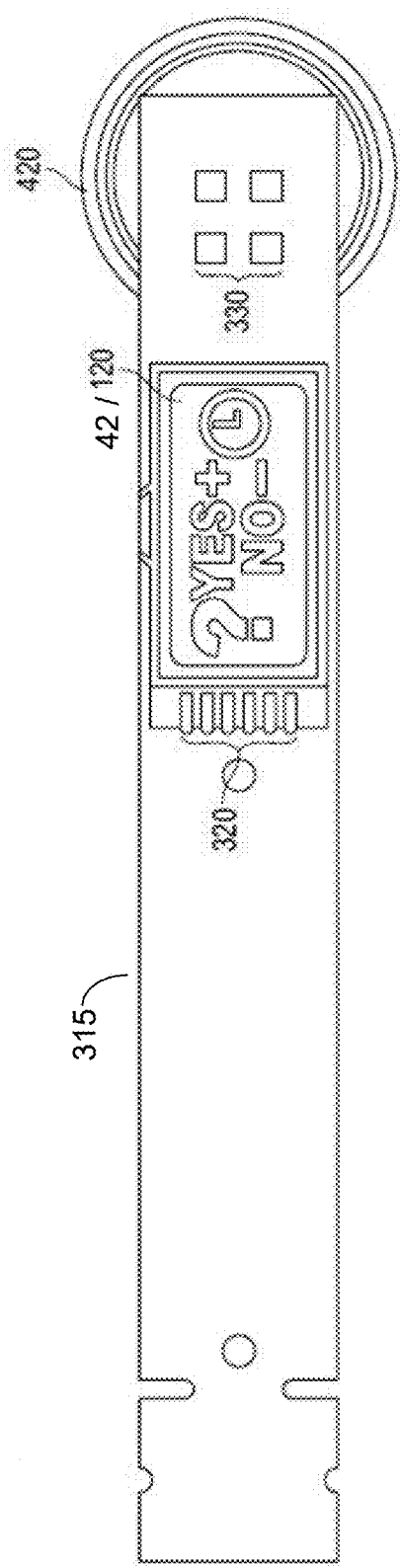
FIG. 3 is a top view of an example of a printed circuit board for a test device according to an implementation of the invention.

FIG. 3 is a top view of a printed circuit board which may be housed in the test devices of FIGS. 1, 2A, and 2B. The display 42 or 120 is coupled with the printed circuit board 315 using one or more signal lines 320. The printed circuit board may include one or more input/output (I/O) terminals 330. The I/O terminals 330 may be used to read or write data from a memory (e.g., collected analyte readings, new program instructions, etc.).

Figure 4:
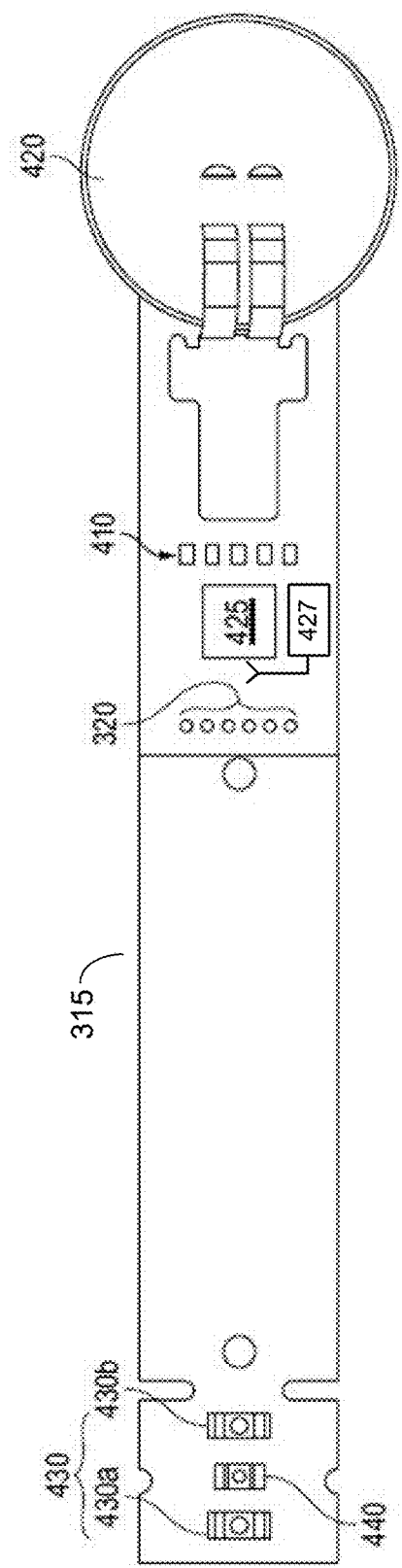
FIG. 4 is a bottom view of an example of a printed circuit board for a test device according to an implementation of the invention.

FIG. 4 is a bottom view of the printed circuit board of FIG. 3. The printed circuit board 315 includes a processor/memory chip 425. The processor chip 425 is coupled with the display 120. In some implementations, the processor chip 425 may be coupled with one or more data I/O pads (not shown) for testing the reader device, data downloads, programming, etc. The memory may be used to store data received or produced by the processor chip 425. The memory may also be used to store instructions to direct operation of the processor chip 425. The printed circuit board 300 may further be coupled to a power source 420. In the example shown in FIG. 4, the power source is a battery, although any other suitable power source may be used such as a kinetic source or a solar source. Discrete components such as resistors and capacitors 410 may also be provided on the printed circuit board 300. To provide the wireless communication capabilities described above, a wireless communication controller 427 may be coupled to the processor/memory chip 425 and an antenna. The wireless communication controller 427 receives data from the processor/memory chip 425 and sends that data wirelessly to the external processing and display device.

The printed circuit board 315 includes one or more sensors 430. In the example shown in FIG. 4, the printed circuit board 315 includes two optical sensors 430a and 430b. In this implementation, the sensors 430 may be phototransistors. In other implementations, the sensors 430 may be one or more photodiodes, electroactive sensors or radioactivity sensors. The sensors may be of the same or different types. The sensors 430 are coupled with the processor chip 425.

The printed circuit board 315 may include an emitter 440. In an implementation including photoelectric sensors 430, the emitter 440 may be a light source such as a light emitting diode (LED). The emitter 440 is preferably configured to selectively emit light at various intensities. In an implementation including photoelectric sensors 430, as shown for example in FIG. 4, the emitter 440 may be located equidistant between the photoelectric sensors 430a and 430b. The emitter 440 may be coupled with the processor chip 425. The light source 440 may illuminate according to a configurable pattern. In an implementation where the light source 440 is coupled with the processor chip 425, the illumination pattern may be controlled by the processor chip 425. The illumination pattern may be controlled by a separate timing circuit (not shown) configured to coordinate instructions provided by the processor chip 425 to the emitter 440.

Figure 5:
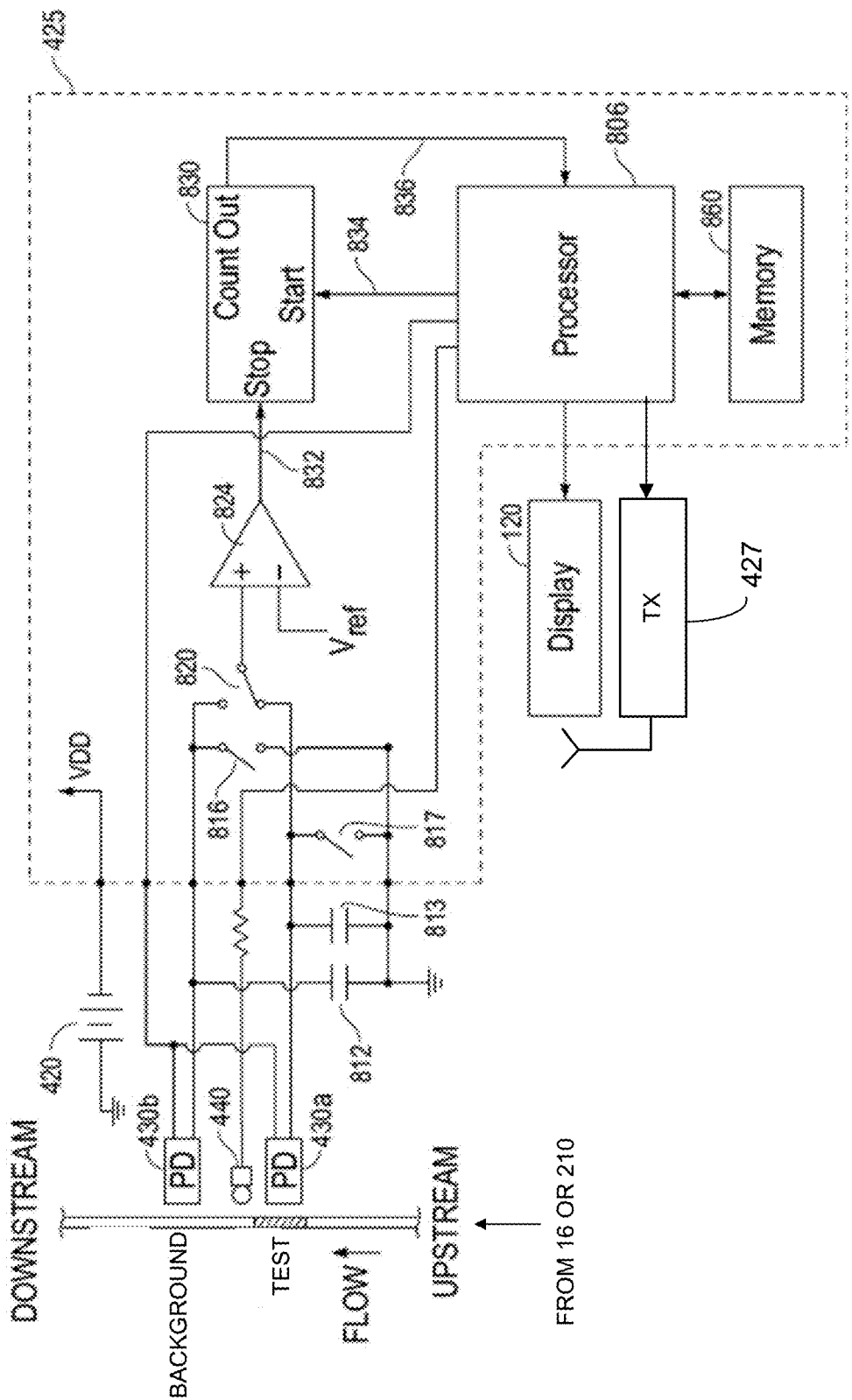
FIG. 5 is a circuit diagram of a test device according to an implementation of the invention.

FIG. 5 is a circuit diagram of an example circuit suitable for use in the test devices of FIGS. 1 and 2, and may be implemented on the circuit board illustrated in FIGS. 3 and 4. This implementation includes photodetectors 430a and 430b as the sensors. Sensor 430a may be positioned substantially over a test region of an integral or removable test strip. Sensor 430b may be positioned over a background region downstream of the test line on the test strip. In this embodiment, no control/reference region is present. As described further below, reflectance measurements are made for these two regions for a time period after a fluid sample is applied to one end of the test strip.

The circuit includes a light emitter 440. The light emitter 440 may be an LED. The light emitter 440 is connected a processing/control circuit 806 that may be in the processor chip 425. The photodetectors 430a and 430b are also each coupled to the processing/control circuit 806 to control initiation of the photodetector operation. The output of photodetector 430a is coupled to capacitor 813, and the output of photodetector 430b is coupled to capacitor 812. The other side of each capacitor is grounded. Each capacitor further has a reset switch 817 and 816 connected across it to selectively discharge the capacitors. In operation, each photodetector output will charge its respective capacitor with its output current. The time required to charge each capacitor to a defined threshold level is a measure of the photodetector output, and thus is a measure of the reflectivity of the test strip in the region under each photodetector.

The time period to charge the capacitor to the threshold may be determined as follows. If photodetector 430a is being measured, LED 440 is switched on, switch 817 is opened, a counter 830 is started, and a switch 820 is used to connect the high side of capacitor 813 to the positive input of a comparator 824. The negative input to the comparator 824 is coupled to a reference voltage, which is advantageously derived from the battery voltage VDD. For example, the reference voltage may be ½ of VDD. The output 832 of the comparator 824 is coupled to a stop input of the counter 830 that stops the counter 830 when the comparator output goes high. As capacitor 813 is charged by the photodetector 430a output, the voltage on the high side of capacitor 813 increases, increasing the voltage input to the positive input of the comparator 824. When this voltage reaches the reference voltage input to the negative side of the comparator 824, the comparator output 832 transitions from low to high. The count value 836, which is a measure of the time between counter start at the beginning of the process and counter stop when the comparator goes high, is fed to the processor 806. In this embodiment, a larger count indicates a longer time for capacitor charging, indicating a lower photodetector output, and therefore a less reflective surface under the photodetector. Once a count for photodetector 430a is acquired, the switch 817 is closed, and the process repeats for photodetector 430b, switch 816, and capacitor 812, with the switch 820 in the other position. Collectively, the elements of the processor chip 425 are connected to one side of a power supply 420. Explicit power transmission traces between the elements of the processor chip 425 have been omitted from FIG. 5. The other side of the power supply 420 is connected to a ground. Processor chip 425 may also include a memory 860 for storing data and instructions as described above.

With such a system, reflectance measurements of regions of the test strip may be made. In many test device applications, such optical measurements are made of areas where chemical reactions take place that are affected by the presence and concentration of a particular substance of interest. Mathematical processing and analysis of these measurements are used to generate a result that is presented to a user of the device. In many implementations, this result is a binary decision indicating either YES, a condition of interest is present, or NO, a condition of interest is not present. Examples include YES/NO results for fertility related testing such as pregnant or not pregnant, ovulating or not ovulating. Other examples include YES/NO results for the presence or absence of an environmental condition such as YES mold is present or NO mold is not present. In some cases, the result is not binary, but may be a set of levels such as high/medium/low, or may be a numerical value that directly states an amount of a detected substance. It will further be appreciated that a large variety of testing protocols may be used, for the same or across a variety of conditions being tested for, each possibly involving different reagents, different measured parameters (optical, electrical, mechanical, or other types of measurement), where each different protocol involves one or both of different measurements and different processing of measurements to generate a result of the test for a user.

In one application of the circuit of FIG. 5, a lateral flow sandwich assay is performed. In this implementation, the test device detects that a test stick is installed and begins taking count values for photodetector 430a (the upstream photodetector) and 430b (the downstream photodetector) at a polling rate. A rate of once per second for the polling rate has been found suitable for reasons that will be described further below. From each pair of counts, the reader computes a measurement value M defined as follows:

$$M = S*((A/B)-(C/D)) \qquad \text{Equation 1}$$

Where
A=initial downstream count value
B=current downstream count value
C=initial upstream count value
D=current upstream count value
S=constant scale factor In use of the device, immediately following test stick installation and application of a fluid sample, the value of M is near zero, because both areas of the test strip under each photodetector have approximately equal reflectances before the fluid sample migrates down the test strip to reach the photodetector regions. Furthermore, the current counts B and D will be about equal to the initial counts A and C, making M about equal to 1−1 which is near zero. When the fluid front of the sample first reaches the upstream detector, the count value D will increase because the test strip in that region becomes less reflective, causing M to increase since A/B is still near 1, but C/D is now less than 1. In a lateral flow sandwich assay, reconstituted gold labeled antibodies and antibody-antigen sandwiches slightly lag the fluid front. When the gold conjugate reaches the region under the upstream photodetector, D increases further, which further increases the value for M. If antigen is present in the fluid sample, gold labeled antibody-antigen sandwiches will be captured at the test region, stopping their further migration down the test strip. When the fluid front and gold labeled antibodies reach the downstream photodetector region, this area will darken also, increasing the count value of B, which decreases the value for M, because A/B becomes smaller than 1. As the assay develops further, most of the gold labeled antibodies that are not part of sandwich complexes and are thus not captured at the test region migrate past the downstream detector region, leaving behind a residual background. After a few minutes, the values for B and D stabilize, stabilizing the value for M to a final value. This value for M will be greater than 0 if the reflectance of the test line is lower than the reflectance of the blank region, which indicates that gold labeled antibody-antigen sandwiches captured at the test line 550 exceed the residual background of gold labeled antibodies in the blank downstream region of the test strip (because D will be larger than B). Higher final values of M indicate higher concentrations of antigen in the fluid sample.

Figure 6:
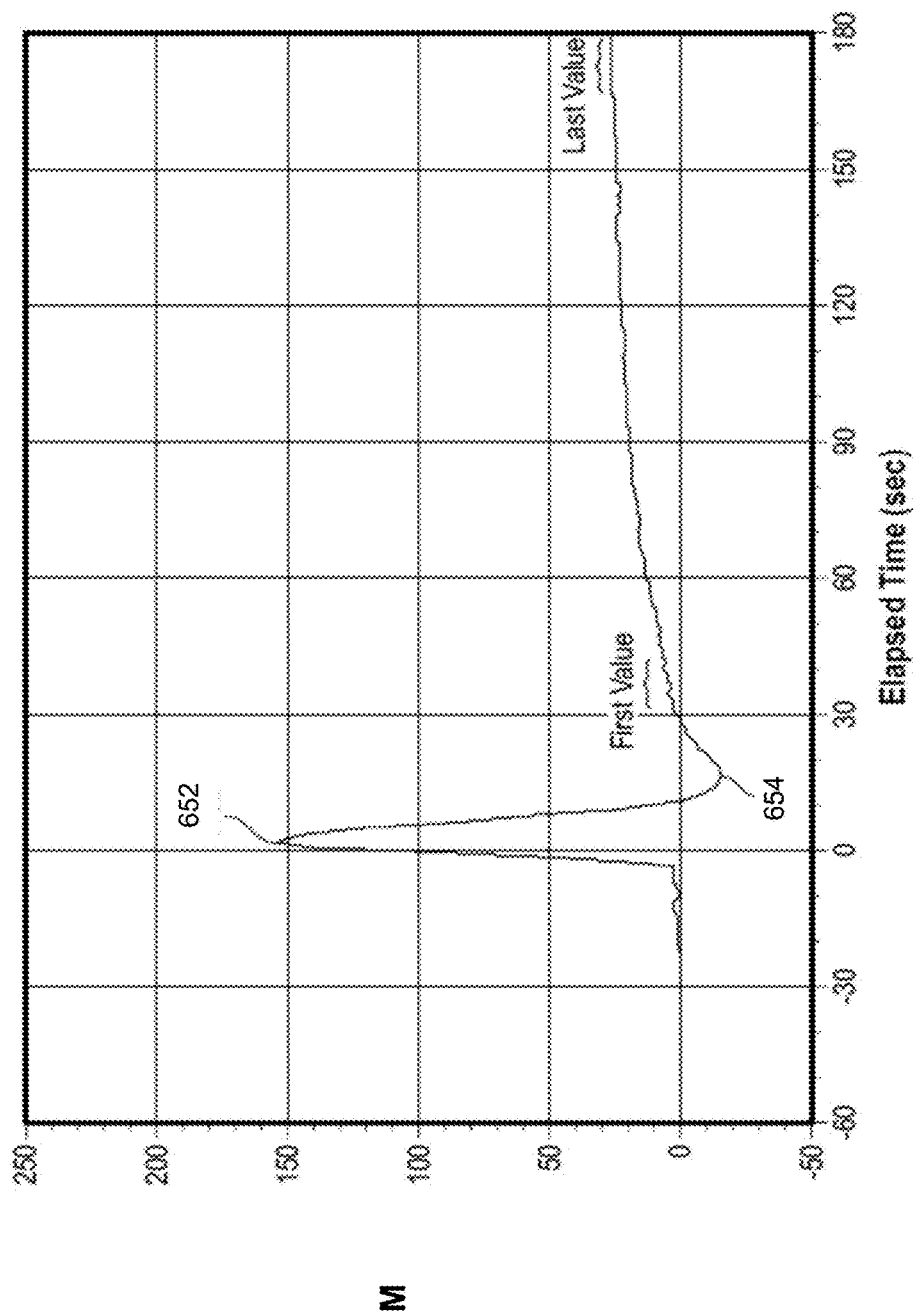
FIG. 6 is an illustration of count values generated by the test device of FIG. 5 during the performance of an assay.

FIG. 6 illustrates M values that may be generated with this protocol during performance of a test. This shows a peak value for M at 652 which occurs when reconstituted gold label has reached the upstream photodetector, but not yet reached the downstream photodetector. A trough 654 is present as reconstituted label flows past the downstream photodetector but before significant development of sandwich binding has occurred at the test line 550. As reagent development at the test line 550 reaches a stable state at or near the last value time of FIG. 6, the concluding M value or values may be processed to generate a result or conclusion that is presented to a user. For example, calibration data stored in the memory 860 may correlate final M values to concentrations of an antigen of interest in predefined units such as PPM or moles/liter. For binary YES/NO results, the final M value or values may be compared to a threshold, and whether M is above or below that threshold determines whether the result presented in YES or NO.

It can be seen with this example that the measurements actually taken by a test device and the processing performed on those measurements to obtain a result presented to a user can vary widely, even though the result does not change. For example, even within the particular protocol described above, the actual numerical values for M that are produced with this algorithm will depend on the value selected for the scale factor S and the sensitivity of the assay materials. Because of this, changes in reagents or mathematical scale factors will require changes in threshold and/or calibration values to produce a correct result. It will also be appreciated that the photodetector currents need not be evaluated with the counter circuit described with reference to FIGS. 5 and 6. The derivation of the parameter M with this circuit described above is only one option. Still further, photodiode currents are not the only way to measure reagent development, so entirely different fundamental physical measurements could be used.

Because of the wide variety of measurement and processing protocols available to reach a result of a given test in a form to be presented to a user, when a test device such as devices 10 and 100 of FIGS. 1 and 2 are provided with communication capabilities to an external processing and display device 50, the result in the form it is to be presented to the user (e.g. a message with two possible values such as 1/0 or YES/NO) is advantageously first generated in the test device 10, 100, and then transmitted as this form of result over the wireless communication channel 46 to the external processing and display device. When the result is transmitted in this manner, the external processing and display device 50 need not perform any interpretation or mathematical manipulation of measurements (e.g. photodiode currents) or intermediate computed values (e.g. the count values or M values described above) to produce a result for presentation to the user. This is in contrast to traditional testing or monitoring devices that send measurement values or intermediate processed measurements (e.g. filtered and/or compressed measurement data) from the test device to an external processing and display device, which then performs additional processing on the received data to generate the result that is presented to a user.

There are a variety of advantages to this communication format. One such advantage is that because the result is generated in the test device 10, 100, the result can be presented on both the display 42/120 of the test device and the display of the external processing and display device 50. In this way, the test device 10, 100 can perform as a stand-alone device to generate a result for a user in the absence of an external processing and display device 50. This is useful in those implementations where the external processing and display device 50 is a "generic" device, wherein as used herein, "generic" means that it is primarily configured and used for purposes other than communicating with test devices 10, 100. In these implementations, because the test devices 10, 100 and external processing and display device 50 are purchased separately, a user may want to utilize a test device 10, 100 as a stand-alone unit because for a variety of reasons an external processing and display device 50 may be unavailable. Another advantage is backward compatibility between external processing and display devices 50 with newly developed test devices 10, 100 that may use different testing protocols internally. This is also useful in those implementations where the external processing and display device 50 is a generic device. In these implementations, the external processing and display device may execute user downloadable application software which, in addition to the device 50 itself, is also acquired by the user separately from the test devices 10, 100. If the manufacturer of the test devices 10, 100 changes reagent chemistry, measurement techniques, component characteristics, or processing algorithms after the user acquires a device 50 and application software, these changes will not affect the ability of the previously acquired device 50 and application software to accurately work with the modified test devices 10, 100. In contrast, if the external processing and display device 50 is receiving measurements or intermediate processed values, new application software tailored for the modified protocols will be required, which is highly inconvenient for the user, and which may in fact cause inaccurate results to be delivered to a user that does not realize that their device 50 is not compatible with the later versions of the test devices 10, 100.

Furthermore, by ensuring the result information is provided, the accuracy of the result is determined by the functionality of the test devices 10, 100. This functionality can be well controlled by the manufacturer of the test devices. If processing is performed in the external processing and display device 50, this can be an uncontrolled environment even if the manufacturer of the test devices 10, 100 also provides the application software on the external processing and display device 50. Especially when the device 50 is a generic device, operating system updates, viruses, hackers, and the like are much more likely to interfere with accurate result generation when the result generation performed in the device 50 than when the device 50 receives the result already in the form for user presentation from the test device 10, 100. Furthermore, in some cases devices which generate a diagnostic output must undergo rigorous certification. It may be desirable to have the test device 10, 100 undergo the certification, and allow the display device to simply receive and present the results.

In some implementations, the only message related to the performance of the test procedure sent from the test device to the processing and display device is a binary YES/NO result, and this result is displayed to the user as a binary YES/NO result accordingly on the processing and display device (and advantageously also on the test device as described above). In some implementations, the only messages related to the performance of the test procedure sent from the test device to the processing and display device are one or more of an indication of test initiation, a binary YES/NO result, and a message that a test error has occurred. In this case, test initiation, the binary YES/NO result, and the error message are displayed if received on the processing and display device (and advantageously also on the test device). In some implementations, one or more of the above messages can be provided along with measurement data or intermediate processed values. In these implementations, the measurement data or intermediate processed values are preferably not used for generating any results that are displayed to a user.

Figure 7:
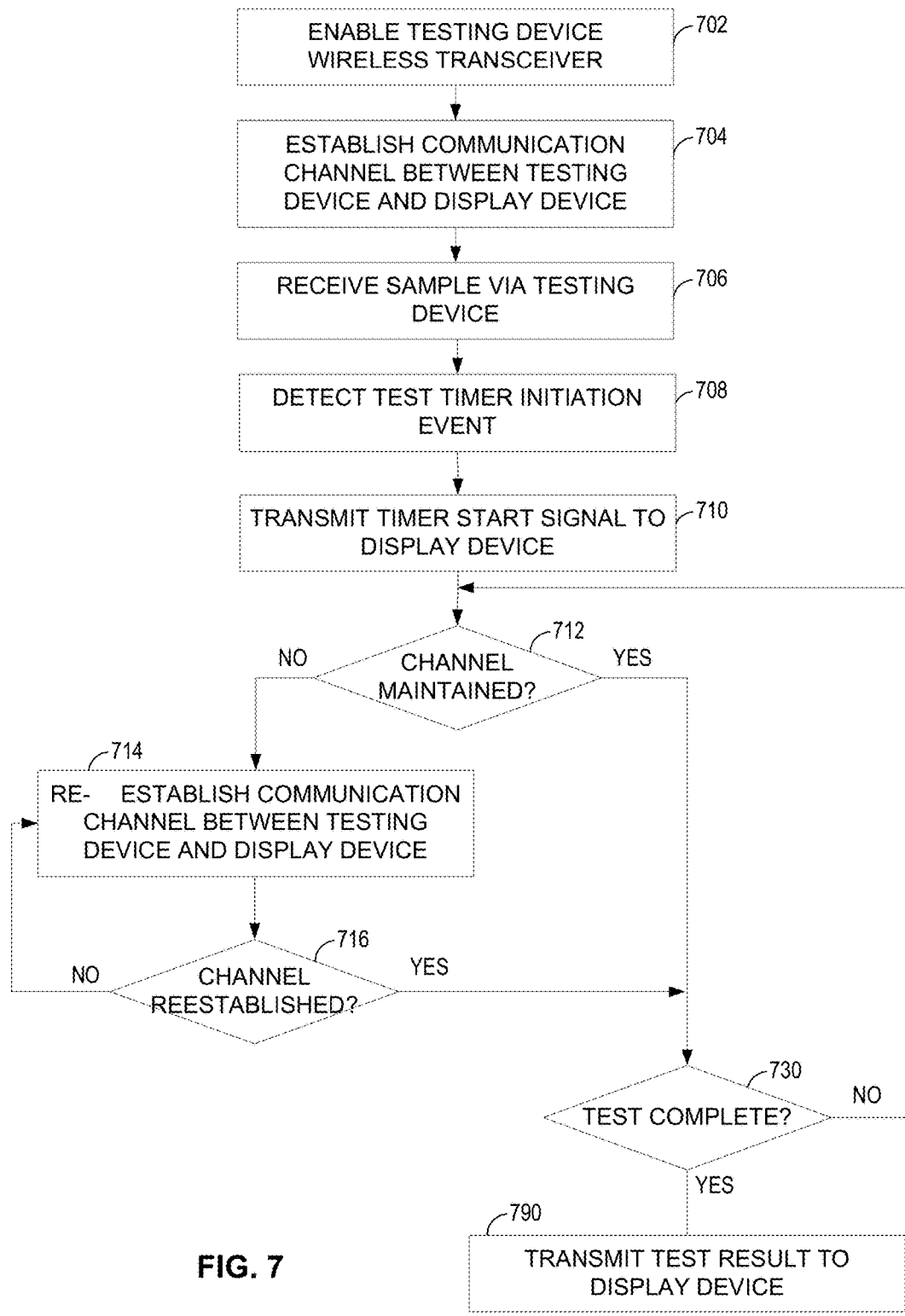
FIG. 7 is a process flow diagram of an example method of testing using a test device and an external processing and display device.

FIGS. 7 and 8 illustrate an example method of testing using a test device and a display device, illustrating some advantageous interactions between a test device and a processing and display device in some implementations. The process shown in FIG. 7 may be implemented in whole or in part by an electronic test device 10, 100 in communication with a processing and display device 50 such as a laptop computer, tablet computer, smartphone, feature phone, set-top-box, smartwatch, personal digital assistant, or other electronic communication device.

Figure 8C:
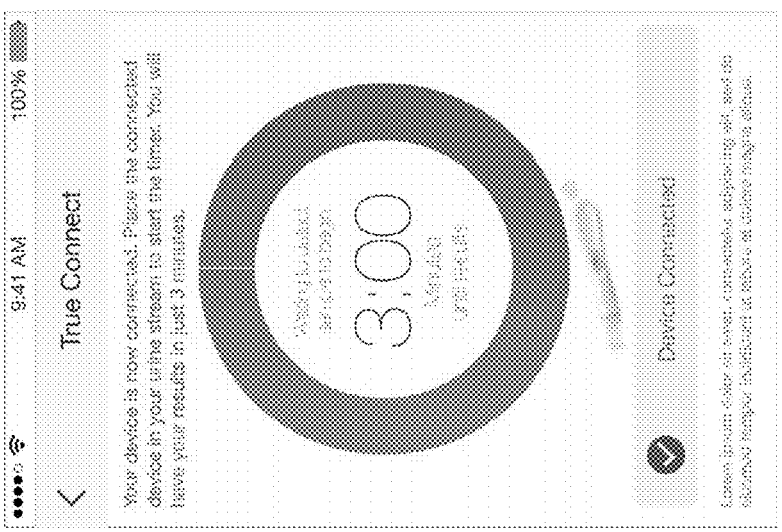
FIGS. 8A-8F are interface diagrams showing example interfaces for a test using a test device and an external processing and display device.
Figure 8B:
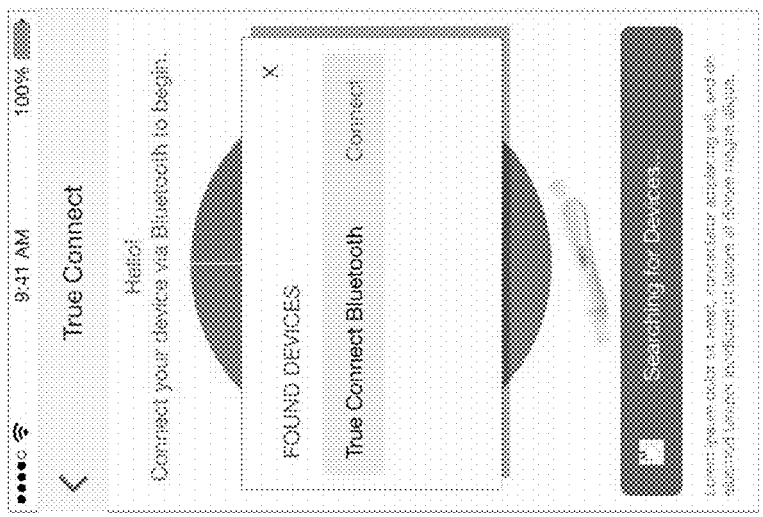
Figure 8A:
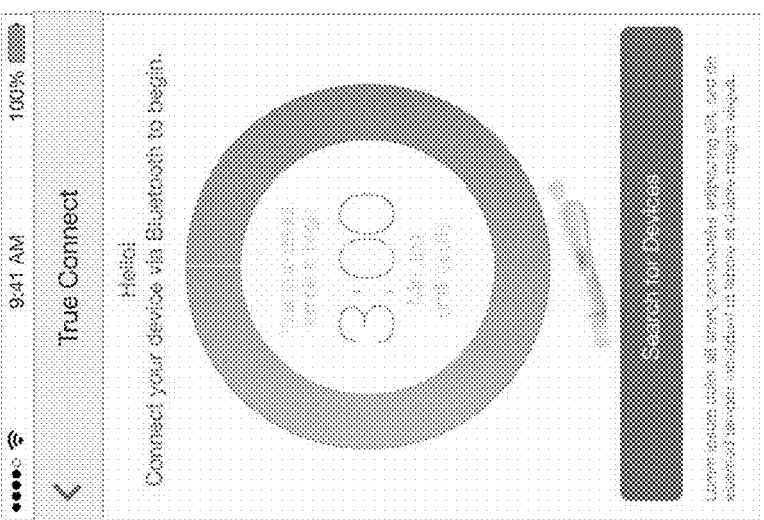

The method begins at block 702 by enabling a wireless transceiver of a test device. Because the test device may be a low power device which remains in a package for a period of time, the test device may be placed in a low power state while in the packaging. Upon removal from the packaging, the test device may include a light sensor which detects ambient light. This detection may cause the test device to increase power in anticipation of performing a test. In such implementations, the increase in power may also cause the enabling of the wireless transceiver. Enabling the wireless transceiver may include providing power to the wireless transceiver. In some implementations, the enabling may also cause the wireless transceiver to begin transmitting a beacon signal, advertising the test device as available for coupling. One example of such a beacon signal may be a pairing request (e.g., BLUETOOTH Secure Simple Pairing). When the test device is first opened or activated, a processing and display device may be located near the test device within range of the beacon signal. During the initial connection process, the application software on the processing and display device 50 may prompt the user to establish a wireless connection with the test device as illustrated in FIGS. 8A and 8B.

At block 704, a communication channel is established between the test device and the display device. The communication channel may be a wireless communication channel such as described above. In some implementations, establishing the communication channel includes exchanging messages between the test device and the display device to ensure mutual agreement to the communication channel. The messages may include exchanging cryptographic information for establishing or communicating via the channel. The establishment may follow a protocol such as the Secure Simple Pairing protocol or other standardized machine-to-machine communication protocol. When the communication channel is established, the application software on the processing and display device 50 may inform the user of the connection and prompt the user to initiate the test as illustrated in FIG. 8C.

At block 706, a sample is received via the test device. The sample may be received via a test stick inserted into the test device.

At block 708, a test timer initiation event is detected. A test timer initiation event is a test event which can be used to start a timer for the test. Examples of the test timer initiation event include detection of a fluid front, detection of application of a sample, detection of receipt of the test strip, obtaining the first measurement indicating the presence or absence of a substance in the sample, or the like. The detection may be performed by the means for conducting the assay such as a light source, sensor, and processor. As one example, the initiation event may be when the M values of FIG. 6 reach their peak value at 1102 indicating that the fluid front of the test sample has reached the detection area of the test strip.

Figures 8D, 8E, 8F:
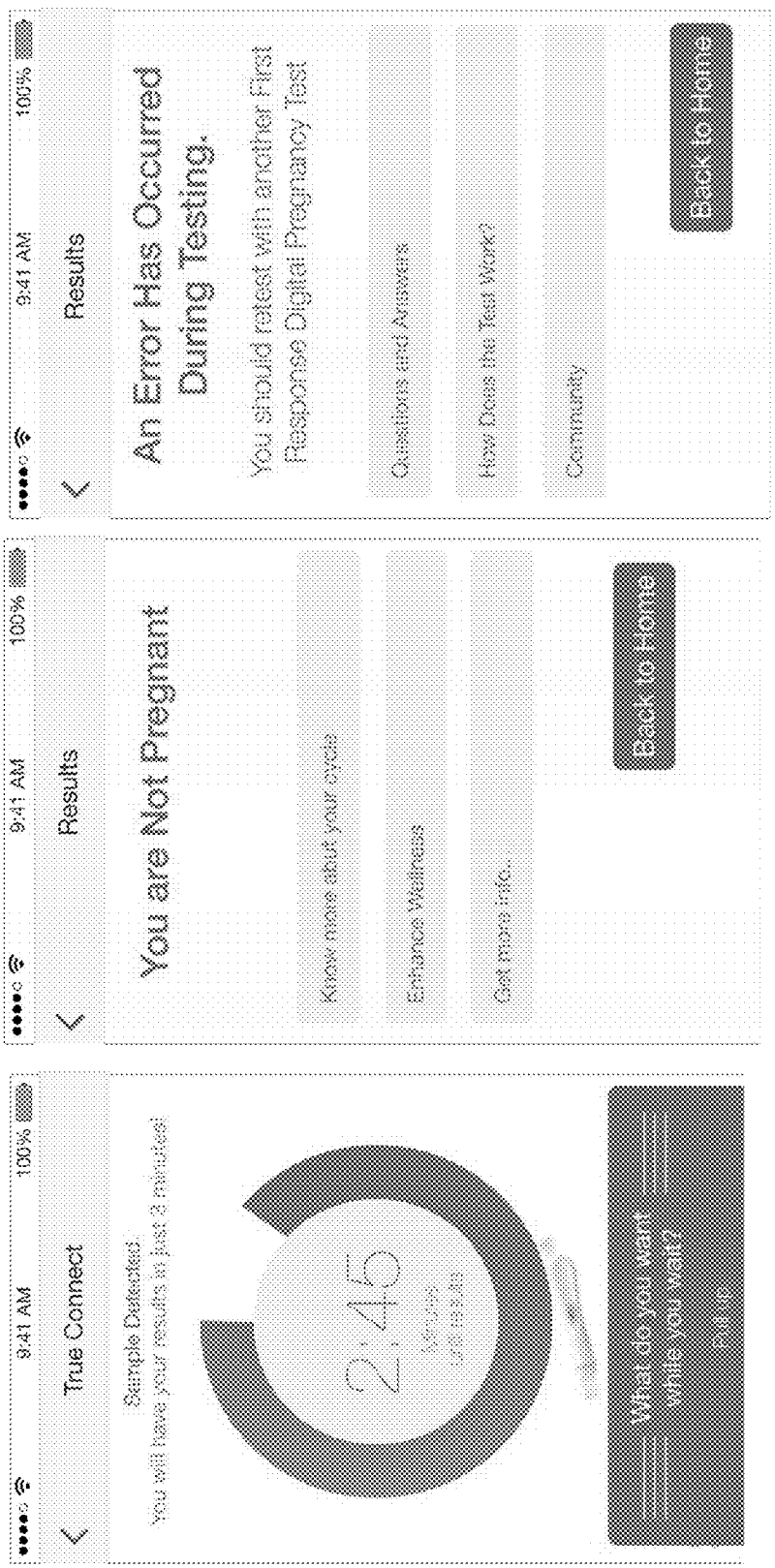

At block 710, a timer start signal is transmitted to the display device. For example, the test device 10, 100 may send a timer start signal to the processing and display device 50 when the peak M value 1102 of FIG. 6 is detected by the test device. The timer start signal causes a timer on the display device to begin tracking time for the test. The timer may be a countdown timer indicating an amount of time until the test is complete. In some implementations, the timer may be a count-up time indicating an elapsed time for the test. By transmitting the timer start signal, the display device and the test device can be synchronized such that the test progress may be tracked. While the timer is in operation, the processing and display device 50 may display the elapsed time or remaining time to the user as illustrated in FIG. 8D.

Once initialized, the processing and display device need not stay in communication with the test device. This may be the case with short-range or low power communication channels. For example, if a woman carrying a smartphone wishes to take a pregnancy test, she may apply the sample in the bathroom. Once applied and her smartphone receives the timer start signal, she may leave the test device in the bathroom and do something else, away from the test device, without losing the timing information.

At block 712, a determination is made as to whether the communication channel is maintained. The determination may be performed using handshake signaling between the test device and the display device. Each device may transmit a message indicating the device is present. If a number of transmissions are left unanswered, the transmitting device may be configured to terminate the channel.

If the channel is maintained, the process continues to decision block 730 where a determination is made as to whether the test is compete. The determination may be performed using measurements. A test may be considered complete if the necessary measurements to generate a result are received. A test may be considered complete if an error condition is detected, such a removal of the strip, flooding of the test strip, light or sensor calibration errors, or the like. If the test is not in a complete state, the process returns to block 712. If the test is complete, at block 790, the test result is transmitted to the external processing and display device. The test result may be displayed via the test device in addition to the transmission to the display device. An example display of a result and an error message on the processing and display device is shown in FIGS. 8E and 8F respectively.

Transmitting the result to the display device allows presentation of the result on the display device. This can provide one non-limiting advantage of making a test device accessible to all persons. For example, if the person is blind, a light display on the test device may not be sufficient to convey the result. However, if the result is transmitted to the display device, an audio message may be triggered indicating the test result.

Figure 16:
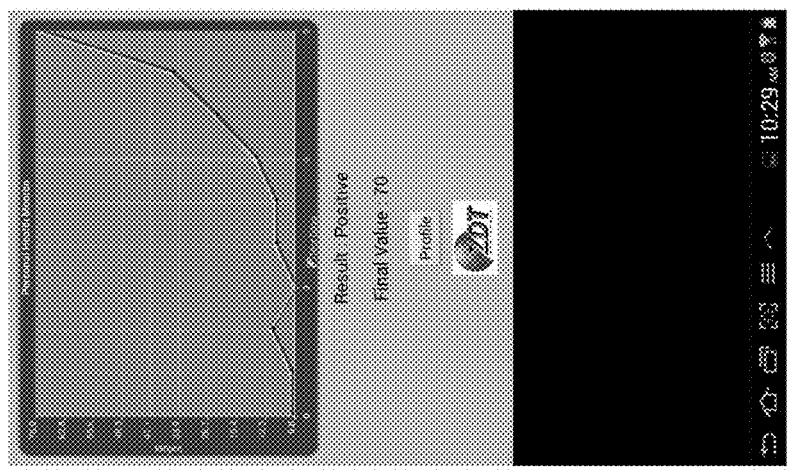
FIG. 16 shows one example of a user interface for presenting a history of test results.

Another non-limiting advantage of transmitting the result to the display device is logging of the test result. In some implementations, it may be desirable to track test results over a period of time. As the test device may be thrown away or otherwise unavailable, it may be desirable to have the results transmitted to the display device for storage. In some implementations, this can allow the display device to present a history of test results. FIG. 16 shows one example of a user interface for presenting a history of test results. The interface may be presented by a personal health monitor application executing on a display device such as a smartphone, tablet computer, laptop computer, or the like. The interface shows test results received over a period of days. The last result may be the test result from the last test in a cycle. For example, in an ovulation/pregnancy detection test, results may be tracked over a period of time to gauge optimal time for conception and, ultimately, pregnancy during a monthly cycle.

Returning to block 712, if the communication channel is not maintained, at block 714, an attempt to re-establish the communication channel is performed. The re-establishment of the communication channel may be performed similarly to the establishing at block 704. At block 716, if the channel was determined to have not been re-established, the process returns to block 714 to try again. If the channel was determined to have been re-established, the process continues to block 730 as described above.

As noted above, FIGS. 8A to 8F are interface diagrams showing example interfaces for a test using a test device and a display device. The interfaces may be presented using a display device. The interfaces shown highlight some of the features which may be implemented using the information received from the test device, such as described in FIG. 7.

FIG. 8A shows an interface diagram of a display device awaiting connection to a test device. The interface may include a control element (e.g., "Search for Devices") to initiate a scan for near-by test devices.

FIG. 8B shows an interface diagram of a display device which has discovered a test device. The discovery may include receiving a pairing message from the test device. As shown in FIG. 8B, the display device includes a control element to affirm establishment of the communication channel with the test device (e.g. "True Connect Bluetooth").

FIG. 8C shows an interface diagram of a display device which has established a communication channel with a test device. The interface includes an indication of the connection status (e.g., "Device Connected" and a check-mark). The interface also includes testing information (e.g., "place the connected device in your urine stream").

FIG. 8D shows an interface diagram of a display device which has detected a timer test initiation event. As shown in FIG. 8D, the event is detecting the sample. As discussed above, the detection may be signaled to the display device from the test device. The timer is also initiated in FIG. 8D, which shows 2 minutes and 45 seconds remaining for the test. Depending on the test, it may be stressful during the period when the user is waiting for the results. FIG. 8D shows an example method the system may use to help relieve this stress. If the "What do you want to do while you wait?" link is accessed, options for playing games, watching an informative video, or playing soothing music, for example, may be presented to the user. One of these options can be selected during the wait time, and the activity can be interrupted when the result is received.

FIG. 8E shows an interface diagram of a display device which has received a test result. In FIG. 8E, the test result is not pregnant. The content presented may be selected based on the test result received from the test device. The content may be further selected using configuration parameters stored on the display device. For example, if a family is hoping for a positive pregnancy result, the result of not pregnant may be presented with a conciliatory tone; while a family that is hoping for a negative result may be provided with a more cheerful message.

FIG. 8F show shows an interface diagram of a display device which has received a test result indicating an error. In some implementations, the error may be identified as part of the result received from the test device. For example, if too much urine was applied, the content presented may include troubleshooting tips for next time. As another example, if the device malfunctioned, the content presented may include a coupon or voucher redeemable for a replacement test device.

Although the system with a wireless communication enabled test device 10, 100 is useful in many applications, in some cases, it is not desirable to add additional circuitry for wireless communication into the test device. However, even in these situations, it may still be desirable to have a way to obtain the results electronically from the test device. Such a method and system is illustrated in FIGS. 9 and 10.

Figure 9:
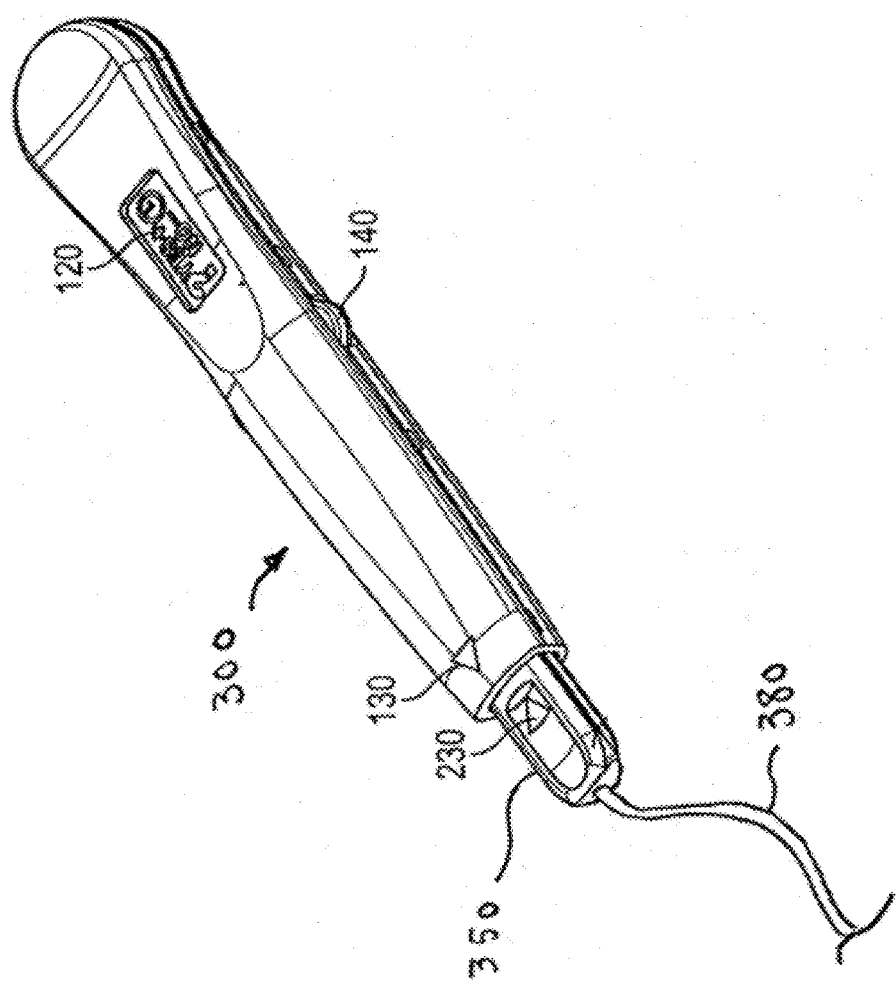
FIG. 9 is a perspective view of an example test device including a data downloading test stick installed.
Figure 10:
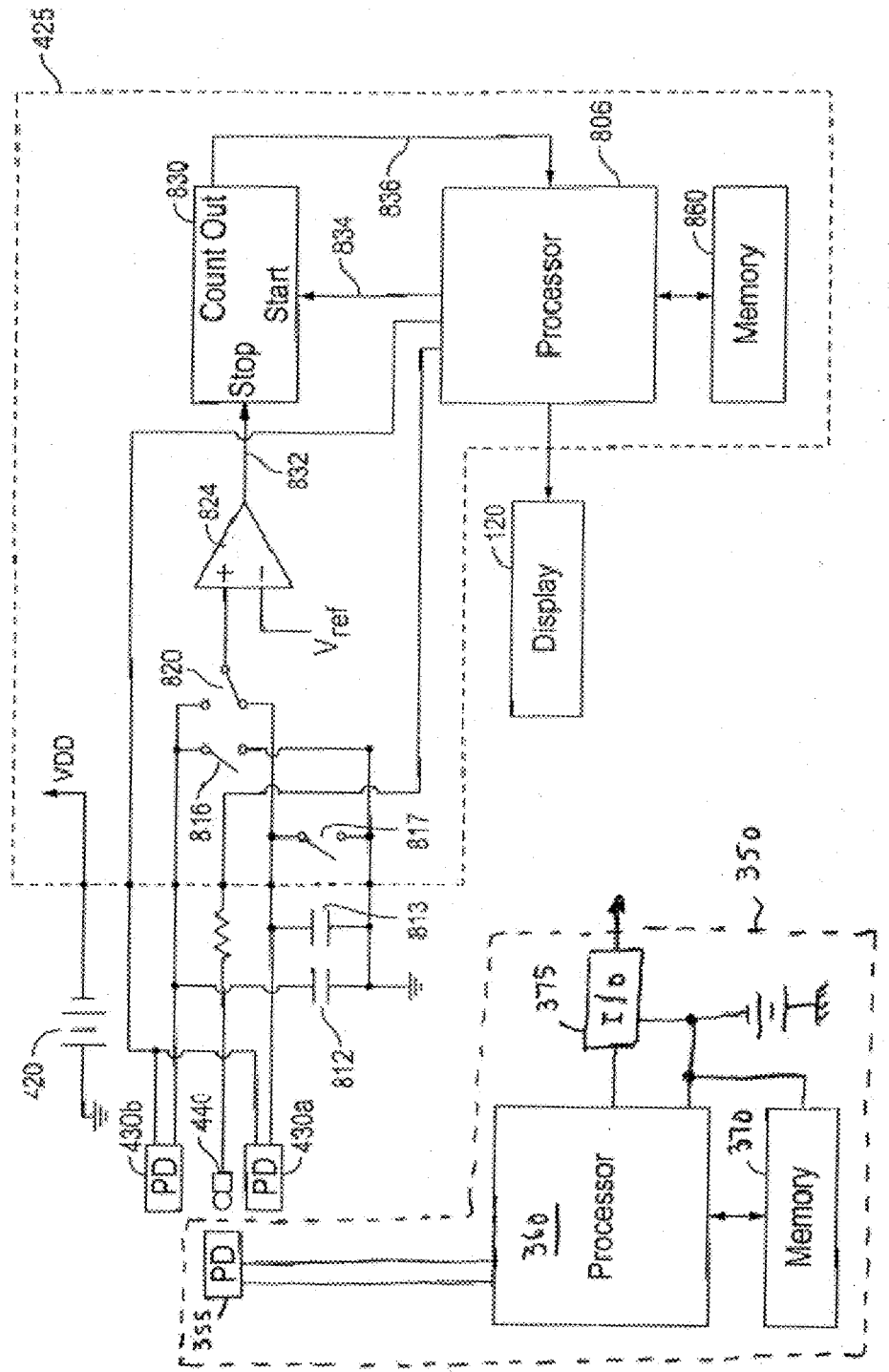
FIG. 10 is a circuit diagram of a test device according to an implementation of the invention.

FIGS. 9 and 10 show a test device 300 similar to that shown in FIG. 2 and FIG. 5 respectively, except without the wireless communication circuit 427. Instead of the wireless communication circuitry 427, a data collector 350 that is shaped similarly to the test sticks which are used with the test device is provided, which may be referred to as a "smart test stick" even though no actual test strip is necessarily provided. The smart test stick fits into the same receiving opening 110 as an actual test stick for performing a test. However, the smart test stick is configured to serve as a data receiver and to download the data from the test device.

As can be seen in FIG. 10, the smart test stick may include a photodiode 355 coupled to a processor 360 which is coupled to a memory 370 and I/O port 375. When the smart test stick is inserted into the test device, the processor 806 in the test device 300 may drive the LED 440 in the test device to transfer data from the test device 300 to the smart test strip 350. The photodiode 355 outputs a current according to the modulation of the LED 440, which is received and decoded by the processor 360. In such a fashion, the smart test stick 350 and the test device may communicate via a light intensity modulation protocol to achieve data transfer.

The smart test stick is further configured to transmit the downloaded data to a PC, a tablet computer, or other data processing device using the I/O port 375. The I/O port may, for example, output data through a cable 380 such as USB or any other data communication format. The smart test stick may thus be implemented as a USB device (e.g., USB 1.0, USB 2.0, USB 3.0, USB 3.1, or other USB standard interface) configured to connect with a USB port (e.g., USB 1.0, USB 2.0, USB 3.0, USB 3.1, or other USB standard interface) on an electronic device such as a personal computer, laptop, or tablet computer. A wireless transmitter could also be provided in the smart test stick as an alternative to a USB or other wired interface, and the electronic device could be any other wireless communication enabled device such as the smartphone discussed above.

The data communication test stick 350 may include electronics formed on a printed circuit board or other suitable medium. The electronics may include one or more photodiodes 355. The processor 360 may be configured to obtain encoded data based on one or more received signals from the photodiode(s) 355. The processor 360 may store received information in the memory 370. For example, results, timing, counts, test device configuration data, and the like may be stored in the memory 370 after receiving it via the LED 440 modulation and photodetector 355. The information stored in the memory 370 may be further transmitted via the I/O port 375. As described above, in some implementations, the I/O port 375 may use a wireless communication interface configured for communication via a standardized protocol such as IEEE 802.15 (e.g., Bluetooth™) or near field communications. In some implementations, the I/O port 375 may be a wired interface such as a USB cable as shown in FIG. 9. The data communication test stick 350 may include an integral power source (not shown) such as a battery. The power source may be coupled with the memory 370, the processor 360, and the I/O port. The smart test stick may alternatively receive power from the I/O port, such as via a USB connection.

The communication need not be limited to only one direction from test device 300 to data communication test stick 350. To also transfer data in the other direction, the smart test stick 350 may also include one or more LEDs itself which may be positioned to align with one or more of the photodetectors 430a, 430b when the smart test stick is installed in the test device 300. These light sources may be connected to and be driven by the processor 360 in a manner similar to the LED 440 in the test device 300. These modulated intensity signals can be received by the photodetectors 430a and/or 430b and decoded by the processor 806 in the test device. Thus, the processor 360 may be configured to modulate a light source to transmit data from the smart test stick to the test device 300. In some implementations, the data may include preferences or variables which can be communicated from the data communication test stick 350 to the test device. For example, the data communication test stick 350 may be inserted into the test device 300 to provide configuration or protocol information for a test to be performed. The configuration may include a test procedural control value such as a detection threshold, illumination wavelength, test time, or any other parameter that would alter the function of the test device so it could perform different test protocols in different situations or for testing for different analytes or conditions.

The LED 440 and photodetectors 430a, 430b may also be used to identify whether a device inserted into opening 110 is a regular test stick on which an assay is to be run or is a smart test stick for data transfer. For this purpose different reflectivities can be provided for regions in the detection area for the two different kinds of sticks, and these differences can be sensed by the processor 806 to determine whether to perform an assay protocol or a data transfer protocol.

In some implementations using the LED modulation scheme for data transfer, the LEDs that are modulated may be LEDs that are visible to a user of the device, and instead of a smart test stick as described above, an externally attachable device is provided to interface in an analogous way with the externally visible LEDs.

Figure 11:
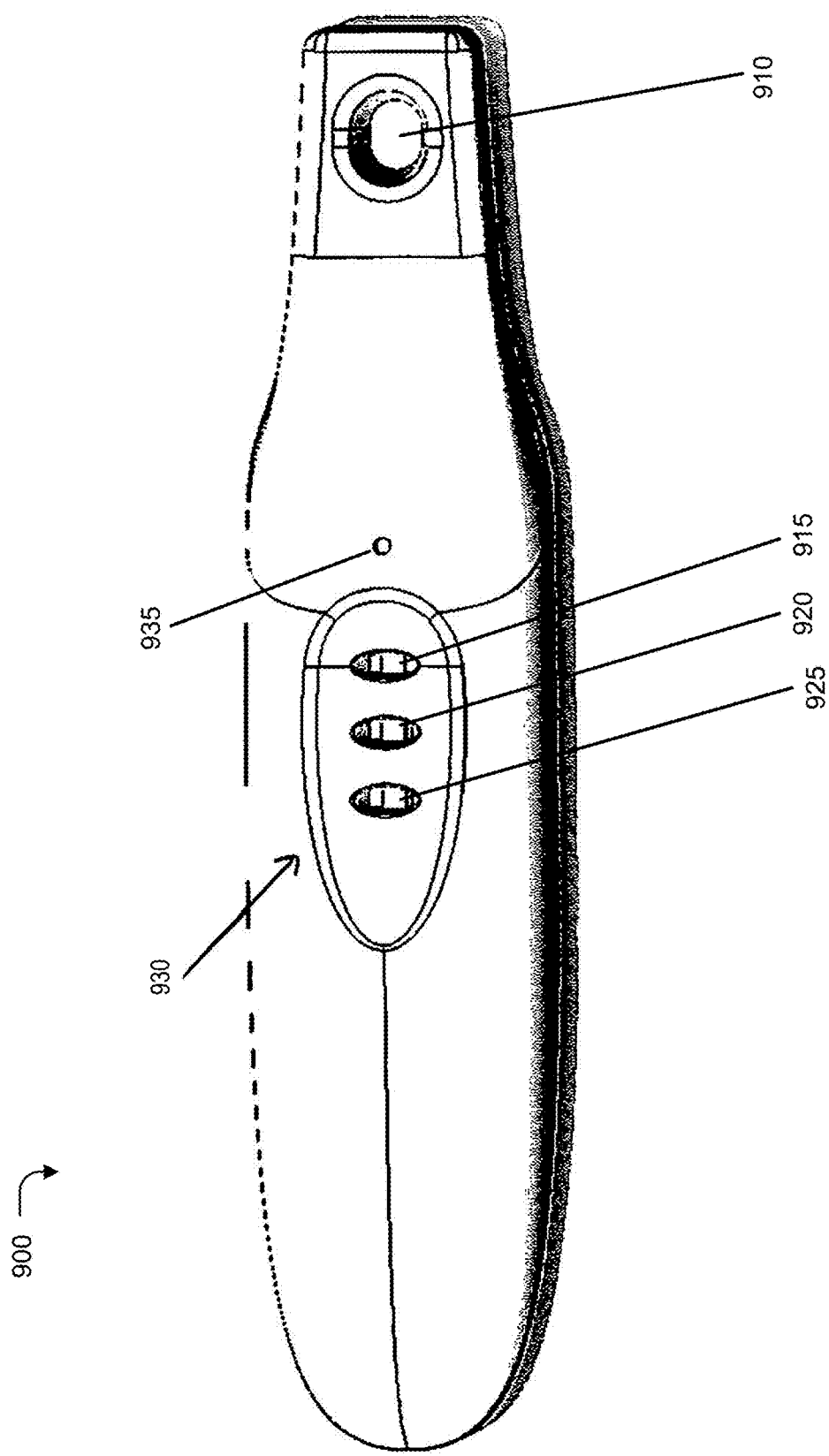
FIG. 11 is a top view of an example test device including a sample receiver.

FIG. 11 is a top view of an example test device including a sample receiver and a mounting structure for such an optical reader. The test device 900 may be a one-time-use device configured to receive a sample via a sample receiver 910. An ambient light portal 935 may be provided to direct ambient light to a light sensor. The light sensor, upon detecting ambient light, may cause the test device 900 to change power state in anticipation of performing a test.

The test device 900 includes three result lights, light 925, light 920, and light 915. The lights may be modulated intensity lights such as LEDs. In some implementations, each light may be a different color (e.g., red, yellow, and green). A test result may be indicated using one or more of the lights 925, 920, and 915. For example, during the test, the yellow light may be turned on or flashed to indicate the test is in progress. If the test positively identifies the substance of interest in the sample, a green light may be turned on. If the test is negative, the red light may be turned on.

While looking at the test device 900 to determine the result may be one way to obtain the result, it may be desirable to obtain the result in a more structured way such as via a result collection device. In such implementation, a result may be provided to the result collection device. For example, if the test device is testing for a hazardous environmental condition in hotel rooms, such as mold, it may be desirable to track in an automated manner where a test was performed and the results obtained to ensure any positively tested rooms are cleaned appropriately. Entering the results manually may result in errors during data entry. Furthermore, the additional information such as location information is not expressly coupled with a given result. Instead, a two-step process may be employed to enter the result and then augment the result with additional data (e.g., location). Because the augmentation may be performed at a different time than the test, the possibility of inaccurate data entry arises again.

To avoid these and other issues with collecting results, it may be desirable to collect the result using an optical results reader. The test device 900 may include a mounting structure 930 to facilitate coupling of the test device 900 with an optical results reader. The mounting structure 930 ensures the optical results reader is properly aligned over the lights 925, 920, and 915. The mounting structure 930 may be further disposed to block ambient light from entering the space between the lights 925, 920, and 915 and an optical results reader when attached to the test device 900.

Figure 12:
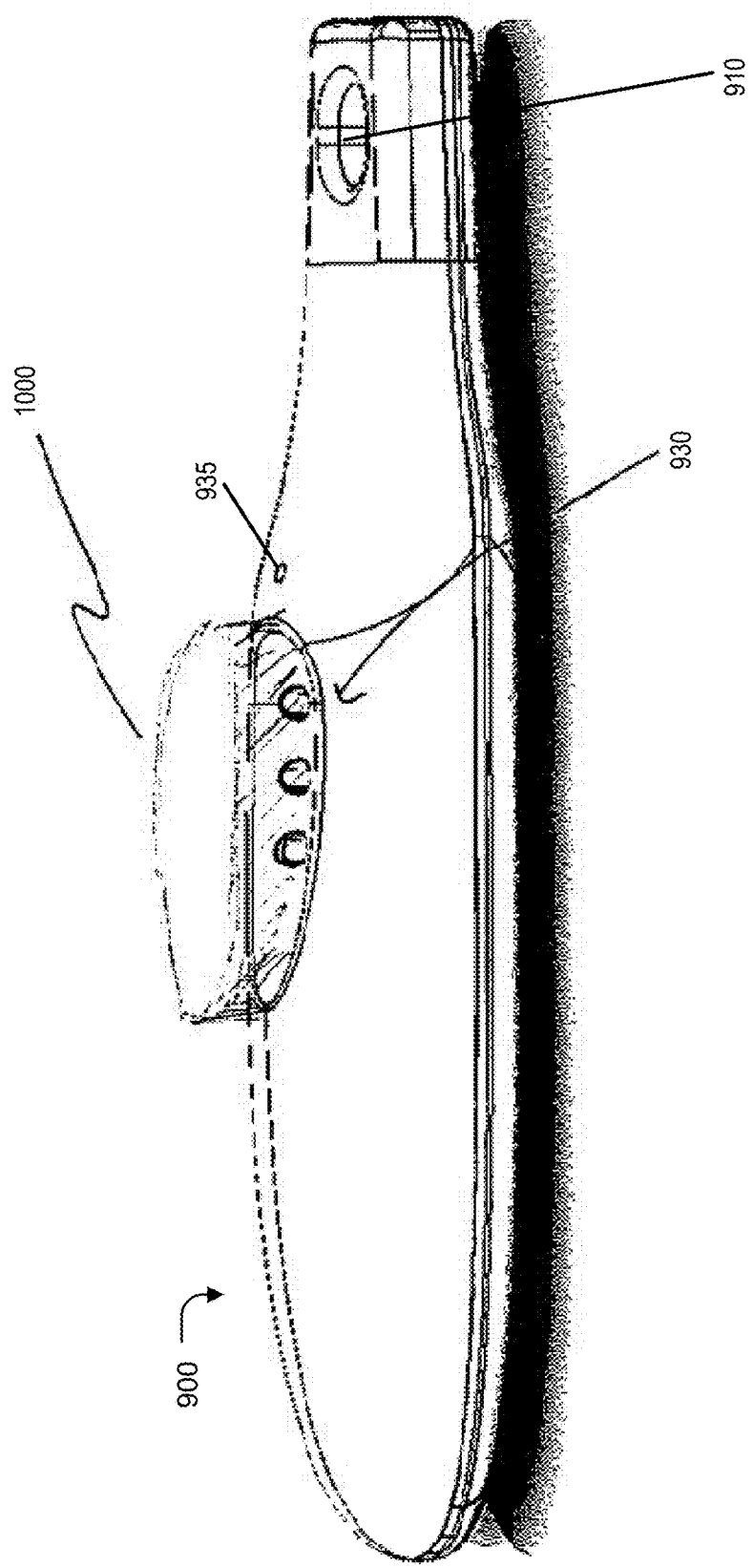
FIG. 12 is a side perspective view of an example test device coupled with an optical results reader.

FIG. 12 is a side perspective view of an example test device coupled with an optical results reader. The optical results reader 1000 is attached to the test device 900 via the mounting structure 930. In some implementations, the attachment may be a snap attachment such that the test device 900 may be lifted by the coupled optical results reader 1000. The optical results reader 1000 is displayed transparently in FIG. 12 to illustrate how the reader may attach to the test device 900 to receive emissions from the lights 925, 920, and 915. The emissions may be modulated light as described in some implementations of this application. Data can be superimposed on the LED(s) at a rate that cannot be seen by the human eye, but can be picked up by the optical results reader.

Figure 13:
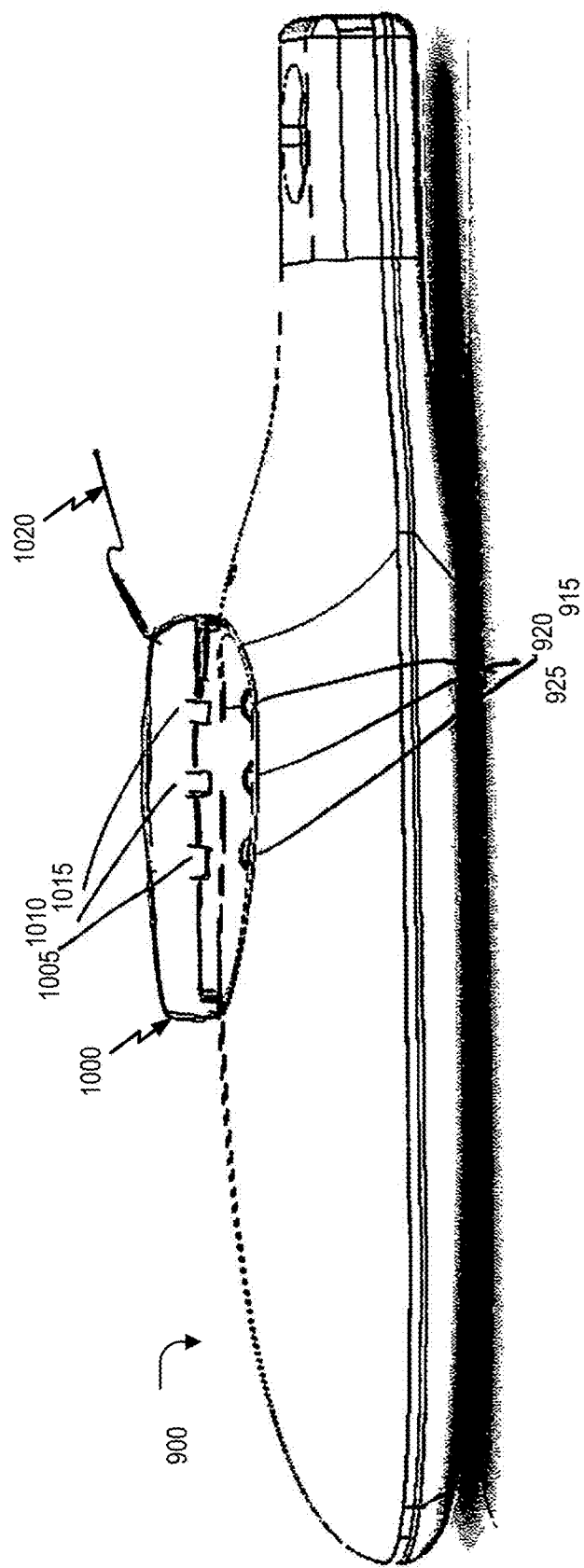
FIG. 13 is a cross-sectional side perspective view of an example test device coupled with an optical results reader.

FIG. 13 is a cross-sectional side perspective view of an example test device coupled with an optical results reader. The cross-section is cut out to show the alignment of the lights 925, 920, and 915 relative to light sensors 1005, 1010, and 1015 included in the optical results reader 1000. As the result is indicated via one or more of the lights 925, 920, and 915, one or more of the light sensors 1005, 1010, and 1015 may detect emitted light. The detection may then be transmitted to a collection device (not shown). In FIG. 13, the transmission may be via wired communication link 1020 such as a USB connection. In some implementations, the optical results reader may include a wireless transceiver configured to transmit the result via a wireless communication channel such as those described above.

Figure 14:
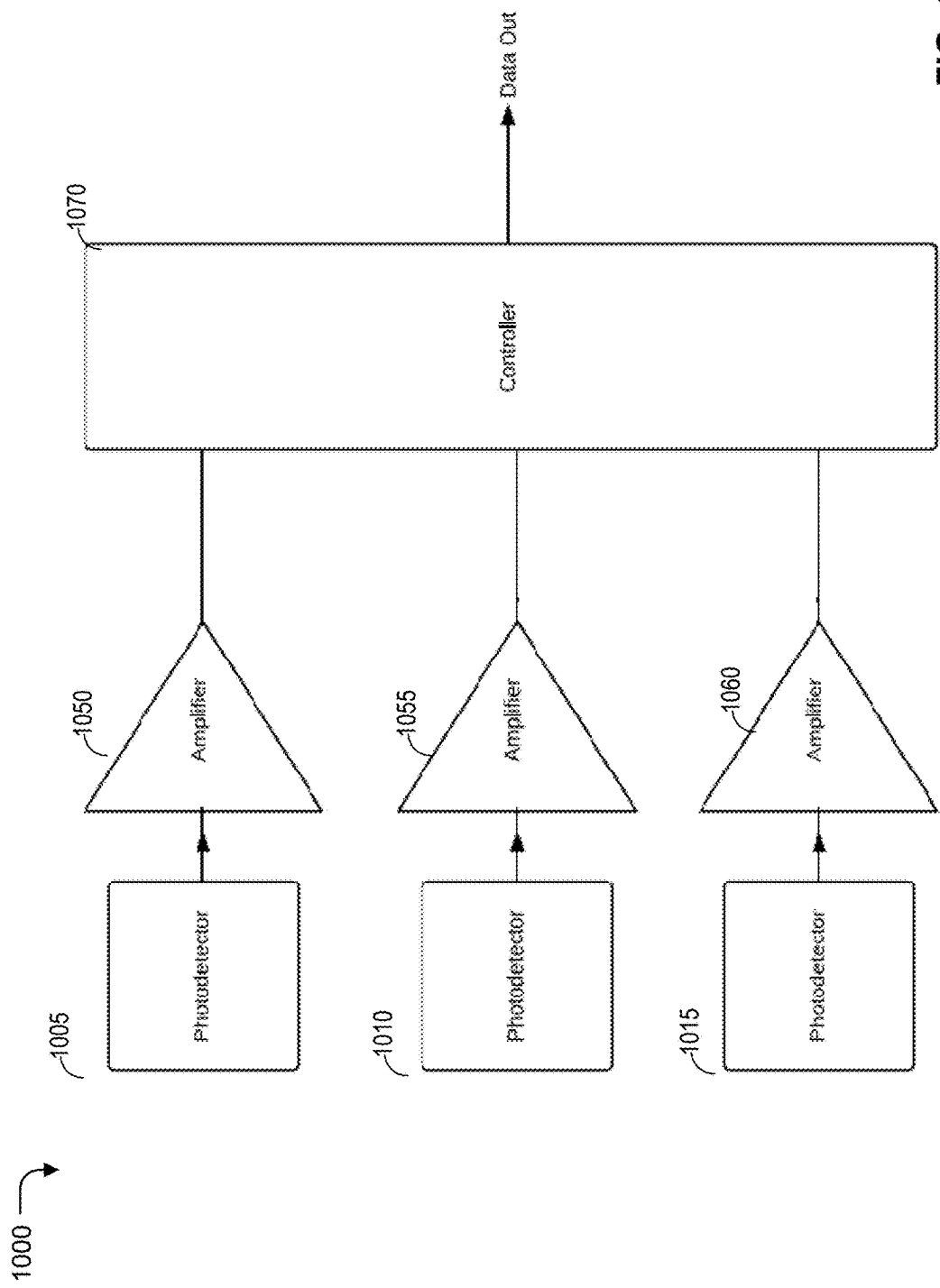
FIG. 14 is a functional block diagram of an example optical results reader.

FIG. 14 is a functional block diagram of an example optical results reader. The optical results reader 1000 shown in FIG. 14 is a simplified reader which may include additional elements to expand or enhance the functionality of the reader 1000 but have been omitted to assist the reader. The light sensors 1005, 1010, and 1015 are implemented in FIG. 14 as photodetectors. Each sensor 1005, 1010, and 1015 is individually coupled to a respective amplifier 1050, 1055, and 1060. The amplifiers 1050, 1055, and 1060 are coupled with a controller 1070. The controller 1070 receives the amplified signals and generates a data output using the received signals. For example, the controller 1070 may determine which lights were turned on by analyzing the associated amplification signals. If the first light (e.g., red)

was turned on, the controller 1070 may provide an output indicating a negative test result. While the reader 1000 shown includes three sensors, other implementations may include fewer or additional sensors. In some implementations, the sensors may be configured as an array of sensors forming a camera. The camera may be included in the optical reader or as part of another electronic device such as a smartphone, tablet computer, digital camera, or other light sensing device.

Figure 15:
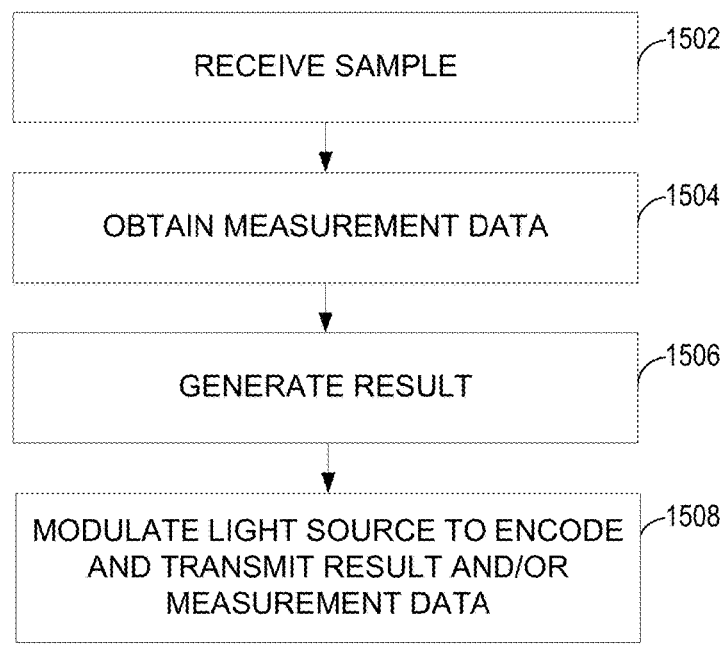
FIG. 15 is a process flow diagram of an example method of testing using a test device and an external processing and display device.

FIG. 15 is a process flow diagram of an example method of communicating results from a test device using the light modulation scheme described above. The method shown in FIG. 15 may be implemented in whole or in part using an electronic test device such as the test device 300 shown in FIGS. 9 through 14.

Referring now to FIG. 15, at block 1502, a sample is received. The sample may be received via a test strip. The sample, as discussed above, may be a liquid sample or other sample suitable for performing an assay using a test device.

At block 1504, measurement data is obtained to determine the presence, absence, or amount of a substance within the sample. The detection may include sampling optical data values over a period of time.

At block 1506, a test result is generated indicating the presence, absence, or amount of the substance. The presence or absence of the substance may be indicated using measurements from block 1504. The test result may be an absolute quantity detected, semi-quantitative value of a quantity detected (e.g., take one or more sensor readings and identify the value in a look-up table correlating the readings to a result value), or a binary (e.g., detected or not detected) value indicating the result. The generation of the test result is performed by the test device.

At block 1508, a light source is modulated to provide an encoding of the test result and/or the measurement data from which the result was derived. For example, a processor may cause a light source included in the test device to modulate in a pattern that encodes the test result value. The pattern may include a preamble indicating data is going to be transmitted such as a predetermined modulated on-off sequence of light. The pattern may then follow with an encoding of the result value. The encoding may be a binary encoding where the result value is converted into binary and each binary digit indicated as light on (binary '1') or light off (binary '0'). The pattern may terminate with an ending or end of transmission sequence such as a predetermined modulated on/off sequence of light (e.g., a predetermined number of consecutive '1' encodings). In some implementations, block 1508 may repeat a predetermined number of times or for a predetermined period of time.

In some implementations, the modulation may include alternatively modulating multiple light sources. For example, in some test devices, two light sources may be included. In such examples, the modulation encoding may be based on light state (e.g., on or off) as well as which light is in a given state. The encoding may include additional information about the test or the test device as described above and below such as a test procedural control value, a test device battery level, an indication of proper sample application, a type of test device, or a test device identifier.

There are also other ways to leverage existing components of test device electronics to transfer result data to an external device. For example, a smartphone may include an application that obtains a picture of a test device's LCD display. The application may be configured to recognize the test result using optical character recognition software on the smartphone. The data obtained can be stored and transmitted by the application to a PC, tablet PC, or other network server.

Also, in addition to leveraging the same detection electronics for both assay execution and data transfer, the detection electronics can be used for other functions as well to improve test performance and provide cost efficiencies. In one innovative aspect, the sensors may be dynamically configured for use allowing the same sensors to be used to for multiple of assays. One background sensor may be configured for use over an entire test strip containing more than one analyte detection. The background sensor can be used as reference or control values for the purpose of comparison for all or a portion of the assays. For example, sensors may be configured to detect more than one test site on a strip and on multiple strips/test sites within the same test device.

Another innovative feature is configuring one or more of the sensors for test strip identification and/or keying. At least one of the sensors can be configured to verify the type of test strip or test cartridge (strip embodiment) that is placed under or inserted into the test device. For example, a contrast in color may be detected based on the color prior to strip insertion and after strip insertion. This contrast may identify the type of test strip and thus the electronic test device may configure one or more elements to perform the test associated with the test strip. This feature enables the use of one test device with more than one type of test strip or test cartridge.

Moreover, the strip embodiment can be mechanically keyed for the electronic circuit found within the electronic device for identification purposes. Keying ensures that test strips of a certain origin and/or quality are used with the test device. This helps improve accuracy and reliability for the test device.

Another innovative use of the existing sensors included in a test device is configuring the sensor to monitor test progress. For example, one or more sensor included in the test device may be configured to monitor the testing progress within the electronic test device to provide assurance to the user that they are performing the test correctly, and that the test device is functioning properly. For tests requiring reagent(s) to be added to sample prior to coming to contact with the test strip (e.g., microfluidic tests), detection sensor (s) can monitor to ensure that required reagents are properly mixed or added within the device for the test strip to function correctly/accurately. The detection sensor(s) may be new sensors integrated into the test device.

Test device sensors may be configured to monitor the test environment. For example, the sensors/LED may be configured to monitor the presence and proper placement (insertion) of the test cartridge prior to starting the testing process. As another example, the removal of the test cartridge, whether during or after use (either intentionally or accidentally), may be monitored to determine if the testing process should be continued. Another example is monitoring for the presence of a crack or an opening within the device's housing or if there is light penetration into the detection/test area. This is critical to prevent inaccurate or false test results.

The test device may also be configured to provide additional information about the test or the test device. For example, a test procedural control value may be communicated with the test result. An example of a procedural control value is total test time, detection thresholds used to generate the result, test events (e.g., fluid front detection), or the like. The test device may provide a test device battery level. This information can be used to identify reusable test devices which may need servicing or replacing. The test device may provide information before, during, or after a test is performed. For example, the battery level may be transmitted prior to testing. This battery level may be insufficient to execute a test and, in such instances, a message indicating the condition may be presented via a display device. As another example, an indication of proper sample application may be transmitted from the test device. This interim progress information can be used to track the test. Information about the test device such as a type of test device indicating the test to be performed can be provided. This allows a display device to properly determine how to present results. For example a test device may be configured for pregnancy detection or bedbug detection. The results for each test may be very different. Accordingly, including the test device type allows a device receiving the result to obtain context for the result. In some implementations, a test device identifier may be provided. The test device identifier may be used to identify a particular test device or device type. This can be useful in assessing whether a device is authentic (e.g., manufactured by and subjected to the quality control of a known producer).

Various connectivity and additional sensor usage features have been described. It will be understood that, in some implementations, it may be desirable to provide a test device including two or more of these features based on the connectivity and assaying requirements of the test device.

As used herein, the terms "determine" or "determining" encompass a wide variety of actions. For example, "determining" may include calculating, computing, processing, deriving, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing, and the like.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As used herein, the terms "provide" or "providing" encompass a wide variety of actions. For example, "providing" may include storing a value in a location for subsequent retrieval, transmitting a value directly to the recipient, transmitting or storing a reference to a value, and the like. "Providing" may also include encoding, decoding, encrypting, decrypting, validating, verifying, and the like.

As used herein, the terms "display" or "displaying" encompass a variety of actions. For example, "displaying" may include presenting in audio form, visual form, or some other form that can be made known to the senses. The term may also include a combination of two or more of the foregoing.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

Disjunctive language such as the phrase "at least one of X, Y, Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

The various operations of methods described above may be performed by any suitable means capable of performing the operations, such as various hardware and/or software component(s), circuits, and/or module(s). Generally, any operations illustrated in the Figures may be performed by corresponding functional means capable of performing the operations.

The various illustrative logical blocks, modules and circuits described in connection with the present disclosure may be implemented or performed with a specially configured processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. The processor may be a microprocessor, but in the alternative, the processor may be a commercially available processor, controller, microcontroller, or state machine configured in accordance with the features described herein. The processor may also be implemented as a combination of specially configured computing devices, e.g., a combination of a DSP and a microprocessor, a plurality of microprocessors, one or more microprocessors in conjunction with a DSP core, or any other such configuration.

In one or more aspects, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a test device such as those described herein. In some aspects computer readable medium may comprise non-transitory computer readable medium (e.g., tangible media). In addition, in some aspects computer readable medium may comprise transitory computer readable medium (e.g., a signal). Combinations of the above should also be included within the scope of computer-readable media.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

Thus, certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Further, it should be appreciated that modules and/or other appropriate means for performing the methods and techniques described herein can be downloaded and/or otherwise obtained by a test device as applicable. For example, such a device can be coupled to a server to facilitate the transfer of means for performing the methods described herein. Alternatively, various methods described herein can be provided via storage means (e.g., RAM, ROM, a physical storage medium such as a compact disc, or floppy disk, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes, and variations may be made in the arrangement, operation, and details of the methods and apparatus described above without departing from the scope of the disclosure.

While the foregoing is directed to aspects of the present disclosure, other and further aspects of the disclosure may be devised without departing from the basic scope thereof.

What is claimed is:

1. A test device comprising:
   assay electronics configured for conducting an assay to generate an assay result indicating the presence, absence, amount, degree, or severity of a chemical, physical, biological, medical, or environmental condition from a sample of material provided to the test device;
   a wireless transmitter coupled to the assay electronics;
   wherein the assay electronics is configured to detect a test initiation event;
   wherein the assay electronics is configured to send a start signal to the wireless transmitter which wirelessly transmits the start signal to an external processing and display device separate from the test device in response to detecting the test initiation event;
   wherein the assay electronics is configured to generate assay measurement data and process that assay measurement data into a single assay result; and
   wherein the assay electronics is configured to send the single assay result to the wireless transmitter which wirelessly transmits the single assay result to the external processing and display device separate from the test device.

2. The test device of claim 1, wherein the wireless transmitter is configured to transmit IEEE 802.15 compliant communications.

3. The test device of claim 1, wherein the assay electronics is further configured to transmit at least one of: a test procedural control value, a test device battery level, an indication of proper sample application, a type of test device, or a test device identifier to the external processing and display device.

4. The test device of claim 1, further comprising a display coupled to the assay electronics, and wherein the assay electronics is configured to both display the single assay result on the display and wirelessly transmit the single assay result to the external processing and display device.

5. A method of testing, the method comprising:
   establishing a wireless communication channel between a test device in a first housing and a display device in a physically separate second housing;
   receiving a sample for testing at the test device;
   detecting, at the test device, a test timer initiation event;
   transmitting a test initiation message from the test device to the display device;
   in response to receiving the test initiation message, initiating and displaying a timer on the display device configured to identify an end time for the testing;
   upon the end time for the testing, obtaining a result of the testing at the display device from the test device; and
   displaying the received result on the display device.

6. The method of claim 5, wherein the test timer initiation event comprises detecting a fluid front during the testing.

7. The method of claim 5, wherein obtaining the test result comprises receiving the result in a result message at the display device.

8. The method of claim 7, wherein the result message is received in response to a result request transmitted from the display device to the test device.

9. The method of claim 5, further comprising displaying a visual representation of the timer on the display device.

10. A testing system comprising:
    a test device including:
      a processor;
      means for receiving a test stick;
      means for conducting an assay configured to:
        detect a test timer initiation event; and
        generate a result indicating the presence or absence of a substance contained in a sample provided via a test stick received via the means for receiving a test stick;
      a first wireless transceiver configured to:
        transmit a test initiation message using the test timer initiation event via a communication channel; and
        transmit the test result via the communication channel;
    an external display device separate from the test device including:
      a second wireless transceiver configured to:
        establish the communication channel with the test device;
        receive the test initiation message from the test device via the communication channel; and
        receive the test result from the test device; and
      a timer, wherein the timer is started in response to receiving the test initiation message;
      a display configured to:
        in response to establishing the communication channel, display a connection status message; and
        display a value of the timer.

11. A handheld, single use, disposable chemical assay device comprising:
a housing;
assay electronics contained within the housing configured to detect a test initiation event and to generate a result for an assay performed during a period of time after the test initiation event;
a display coupled to the housing and the assay electronics configured to display the result of the assay received from the assay electronics;
a wireless transmitter contained within the housing;
wherein the assay electronics and the wireless transmitter are configured to transmit both a start signal in response to the detection of the test initiation event and the result of the assay performed after the test initiation event to an external processing and display device.

* * * * *